(12) United States Patent
Knopfmacher et al.

(10) Patent No.: US 12,276,634 B2
(45) Date of Patent: *Apr. 15, 2025

(54) APPARATUS, SYSTEMS, AND METHODS FOR DETERMINING SUSCEPTIBILITY OF MICROORGANISMS TO ANTI-INFECTIVES

(71) Applicant: Avails Medical, Inc., Menlo Park, CA (US)

(72) Inventors: Oren S. Knopfmacher, San Francisco, CA (US); Meike Herget, Woodside, CA (US); August Estabrook, South San Francisco, CA (US); Nitin K. Rajan, Palo Alto, CA (US); Michael D. Laufer, Menlo Park, CA (US)

(73) Assignee: Avails Medical, Inc., Menlo Park, CA (US)

( * ) Notice: Subject to any disclaimer, the term of this patent is extended or adjusted under 35 U.S.C. 154(b) by 317 days.

This patent is subject to a terminal disclaimer.

(21) Appl. No.: 17/806,206

(22) Filed: Jun. 9, 2022

(65) Prior Publication Data

US 2022/0317087 A1 Oct. 6, 2022

Related U.S. Application Data

(63) Continuation of application No. 16/716,945, filed on Dec. 17, 2019, now Pat. No. 11,385,200, which is a continuation of application No. PCT/US2018/031418, filed on May 7, 2018.

(60) Provisional application No. 62/525,671, filed on Jun. 27, 2017.

(51) Int. Cl.
*C12Q 1/18* (2006.01)
*G01N 27/416* (2006.01)

(52) U.S. Cl.
CPC ........... *G01N 27/4168* (2013.01); *C12Q 1/18* (2013.01)

(58) Field of Classification Search
CPC ......... C12Q 1/18; C12Q 1/06; G01N 27/4168
See application file for complete search history.

(56) References Cited

U.S. PATENT DOCUMENTS

| | | |
|---|---|---|
| 3,743,581 A | 7/1973 | Cady et al. |
| 4,200,493 A | 4/1980 | Wilkins et al. |
| 4,209,586 A * | 6/1980 | Noller ............ C12M 41/36 435/287.1 |
| 4,236,893 A | 12/1980 | Rice |
| 4,314,821 A | 2/1982 | Rice |
| 4,321,322 A | 3/1982 | Ahnell |
| 4,448,534 A | 5/1984 | Wertz et al. |
| 4,615,978 A | 10/1986 | Sandine et al. |
| 4,735,906 A | 4/1988 | Bastiaans |
| 4,767,719 A | 8/1988 | Finlan |
| 4,789,804 A | 12/1988 | Karube et al. |
| 4,822,566 A | 4/1989 | Newman |
| 4,965,193 A | 10/1990 | Chen |
| 4,977,247 A | 12/1990 | Fahnestock et al. |
| 5,064,756 A | 11/1991 | Carr et al. |
| 5,077,210 A | 12/1991 | Eigler et al. |
| 5,111,221 A | 5/1992 | Fare et al. |
| 5,172,332 A | 12/1992 | Hungerford et al. |
| 5,182,005 A | 1/1993 | Schwiegk et al. |
| 5,218,304 A | 6/1993 | Kinlen et al. |
| 5,356,782 A | 11/1994 | Moorman et al. |
| 5,447,845 A | 9/1995 | Chu et al. |
| 5,821,399 A | 10/1998 | Zelin |
| 5,922,537 A | 7/1999 | Ewart et al. |
| 6,280,586 B1 | 8/2001 | Wolf et al. |
| 6,368,795 B1 | 4/2002 | Hefti |
| 6,391,558 B1 | 5/2002 | Henkens et al. |
| 6,391,577 B1 | 5/2002 | Mikkelsen et al. |
| 6,548,263 B1 | 4/2003 | Kapur et al. |
| 6,548,311 B1 | 4/2003 | Knoll |
| 6,780,307 B2 | 8/2004 | Kidwell |

(Continued)

FOREIGN PATENT DOCUMENTS

| | | |
|---|---|---|
| CN | 101057143 | 10/2007 |
| CN | 101852765 | 10/2010 |

(Continued)

OTHER PUBLICATIONS

Vila et al. 2016 (*Escherichia coli*: an old friend with new tidings; FEMS Microbiology Reviews; 40: 437-463). (Year: 2016).*

(Continued)

*Primary Examiner* — Mary Maille Lyons
(74) *Attorney, Agent, or Firm* — Levine Bagade Han LLP

(57) ABSTRACT

Various devices, systems and methods of detecting a susceptibility of one or more infectious agents to one or more anti-infectives are described herein. In one embodiment, a method of detecting the susceptibility of the infectious agents to the anti-infectives involves introducing a sample comprising the infectious agents to a filter comprising a filter surface. The filter surface can be configured to capture the infectious agents in the sample. The method can also involve introducing a solution to the filter surface such that the solution is in fluid communication with the infectious agents captured on the filter surface. The solution can comprise nutrients and one or more anti-infectives. The method can further involve monitoring an oxidation reduction potential (ORP) of the solution using one or more parameter analyzers coupled to a sensor currently in fluid communication with the solution to assess the susceptibility of the infectious agents to the anti-infectives.

20 Claims, 12 Drawing Sheets

(56) References Cited

U.S. PATENT DOCUMENTS

| | | |
|---|---|---|
| 6,863,792 B1 | 3/2005 | Madou et al. |
| 7,745,272 B2 | 6/2010 | Van De Walle et al. |
| 8,508,100 B2 | 8/2013 | Lee et al. |
| 8,728,844 B1 | 5/2014 | Liu et al. |
| 9,377,456 B1 | 6/2016 | Herget et al. |
| 9,702,847 B2 | 7/2017 | Herget et al. |
| 9,766,201 B2 | 9/2017 | Herget et al. |
| 9,944,969 B2 | 4/2018 | Knopfmacher et al. |
| 9,963,733 B2 | 5/2018 | Knopfmacher et al. |
| 10,060,916 B2 | 8/2018 | Knopfmacher |
| 10,174,356 B2 | 1/2019 | Knopfmacher et al. |
| 10,254,245 B2 | 4/2019 | Knopfmacher et al. |
| 11,385,200 B2 * | 7/2022 | Knopfmacher .... G01N 27/4168 |
| 11,655,494 B2 | 5/2023 | Knopfmacher et al. |
| 2002/0127623 A1 | 9/2002 | Minshull et al. |
| 2003/0073071 A1 | 4/2003 | Fritz et al. |
| 2003/0109056 A1 | 6/2003 | Vossmeyer et al. |
| 2003/0119208 A1 | 6/2003 | Yoon et al. |
| 2004/0195098 A1 | 10/2004 | Broadley et al. |
| 2005/0116263 A1 | 6/2005 | Lu et al. |
| 2006/0088839 A1 | 4/2006 | Matsui et al. |
| 2006/0102935 A1 | 5/2006 | Yitzchaik et al. |
| 2006/0197118 A1 | 9/2006 | Migliorato et al. |
| 2006/0246426 A1 | 11/2006 | Woodbury et al. |
| 2006/0286548 A1 | 12/2006 | Liposky |
| 2007/0037225 A1 | 2/2007 | Metzger et al. |
| 2007/0054396 A1 | 3/2007 | Peppers et al. |
| 2007/0072187 A1 | 3/2007 | Blok et al. |
| 2008/0012007 A1 | 1/2008 | Li et al. |
| 2008/0199863 A1 | 8/2008 | Haake et al. |
| 2009/0008247 A1 | 1/2009 | Chen et al. |
| 2009/0020438 A1 | 1/2009 | Hodges |
| 2009/0273354 A1 | 11/2009 | Dhirani et al. |
| 2010/0025660 A1 | 2/2010 | Jain et al. |
| 2010/0137143 A1 | 6/2010 | Rothberg et al. |
| 2010/0194409 A1 | 8/2010 | Gao et al. |
| 2011/0068372 A1 | 3/2011 | Ren et al. |
| 2011/0306032 A1 | 12/2011 | Galiano et al. |
| 2012/0032235 A1 | 2/2012 | Bikumandla |
| 2012/0077692 A1 | 3/2012 | Hassibi et al. |
| 2012/0088682 A1 | 4/2012 | Rothberg et al. |
| 2012/0143027 A1 | 6/2012 | Phillips et al. |
| 2012/0153262 A1 | 6/2012 | Paranjape et al. |
| 2012/0153407 A1 | 6/2012 | Chang et al. |
| 2012/0165246 A1 | 6/2012 | Lindner et al. |
| 2012/0168306 A1 | 7/2012 | Hassibi et al. |
| 2012/0208291 A1 | 8/2012 | Davis et al. |
| 2012/0214172 A1 | 8/2012 | Chen et al. |
| 2012/0261274 A1 | 10/2012 | Rearick et al. |
| 2012/0256166 A1 | 11/2012 | Chen et al. |
| 2012/0279859 A1 | 11/2012 | Rothberg et al. |
| 2013/0089883 A1 | 4/2013 | Dallenne et al. |
| 2013/0089932 A1 | 4/2013 | Wu et al. |
| 2013/0096013 A1 | 4/2013 | Esfandyarpour et al. |
| 2013/0105868 A1 | 5/2013 | Kalnitsky et al. |
| 2013/0217063 A1 | 8/2013 | Metzger et al. |
| 2014/0011218 A1 | 1/2014 | Han et al. |
| 2014/0057339 A1 | 2/2014 | Esfandyarpour et al. |
| 2014/0134656 A1 | 5/2014 | Dortet et al. |
| 2014/0186215 A1 | 6/2014 | Shinta et al. |
| 2014/0191294 A1 | 7/2014 | Bikumandla et al. |
| 2014/0231256 A1 | 8/2014 | Packingham et al. |
| 2014/0349005 A1 | 11/2014 | Everett et al. |
| 2015/0355129 A1 | 12/2015 | Knopfmacher |
| 2016/0039657 A1 | 2/2016 | Jain et al. |
| 2016/0068417 A1 | 3/2016 | Buschmann |
| 2016/0187332 A1 | 6/2016 | Herget et al. |
| 2016/0187334 A1 | 6/2016 | Herget et al. |
| 2016/0208306 A1 | 7/2016 | Pollak et al. |
| 2016/0209356 A1 | 7/2016 | Herget et al. |
| 2016/0266102 A1 | 9/2016 | Knopfmacher |
| 2017/0058313 A1 | 3/2017 | Knopfmacher et al. |
| 2017/0059508 A1 | 3/2017 | Knopfmacher et al. |
| 2017/0212075 A1 | 7/2017 | Knopfmacher et al. |
| 2017/0336348 A1 | 11/2017 | Herget et al. |
| 2017/0336384 A1 | 11/2017 | Ino et al. |
| 2017/0342459 A1 | 11/2017 | Knopfmacher et al. |
| 2018/0195106 A1 | 7/2018 | Knopfmacher et al. |
| 2018/0364221 A1 | 12/2018 | Knopfmacher |
| 2019/0046984 A1 | 2/2019 | Kelley et al. |
| 2019/0136290 A1 | 5/2019 | Knopfmacher et al. |
| 2019/0293529 A1 | 9/2019 | Rajan et al. |
| 2019/0310214 A1 | 10/2019 | Herget et al. |
| 2020/0150082 A1 | 5/2020 | Knopfmacher et al. |
| 2020/0224241 A1 | 7/2020 | Knopfmacher et al. |
| 2021/0325371 A1 | 10/2021 | Rajan et al. |
| 2023/0250463 A1 * | 8/2023 | Knopfmacher ........ G01N 15/06 435/32 |

FOREIGN PATENT DOCUMENTS

| | | |
|---|---|---|
| CN | 105473740 | 4/2016 |
| CN | 107205808 | 9/2017 |
| EP | 0235024 | 9/1987 |
| EP | 1460130 | 9/2004 |
| EP | 2172767 | 4/2010 |
| JP | 1988-066454 | 3/1988 |
| JP | 1996-0886771 | 4/1996 |
| JP | 2002-112761 | 4/2002 |
| JP | 2003-052392 | 2/2003 |
| JP | 2005-287452 | 10/2005 |
| JP | 2006-511818 | 4/2006 |
| JP | 2011-58900 | 3/2011 |
| JP | 2011-062195 | 3/2011 |
| JP | 2012-024085 | 2/2012 |
| JP | 2011-085038 | 11/2012 |
| WO | WO 1992/009700 | 6/1992 |
| WO | WO 2003/044530 | 5/2003 |
| WO | WO 2003/052097 | 6/2003 |
| WO | WO 2004/077052 | 9/2004 |
| WO | WO 2006/102695 | 10/2006 |
| WO | WO 2007/035814 | 3/2007 |
| WO | WO 2009/021908 | 2/2009 |
| WO | WO 2010/062001 | 6/2010 |
| WO | WO 2012/078340 | 6/2012 |
| WO | WO 2013/096404 | 6/2013 |
| WO | WO 2014/080292 | 5/2014 |
| WO | WO 2014/134431 | 9/2014 |
| WO | WO 2015/077632 | 5/2015 |
| WO | WO 2015/188002 | 12/2015 |
| WO | WO 2016/005743 | 1/2016 |
| WO | WO 2016/028233 | 2/2016 |
| WO | WO 2016/044417 | 3/2016 |
| WO | WO 2016/061453 | 4/2016 |
| WO | WO 2016/065475 | 5/2016 |
| WO | WO 2016/109569 | 7/2016 |
| WO | WO 2017/035393 | 3/2017 |
| WO | WO 2017/107333 | 6/2017 |
| WO | WO 2017/132095 | 8/2017 |
| WO | WO 2017/209839 | 12/2017 |
| WO | WO 2018/111234 | 6/2018 |
| WO | WO 2018/145338 | 8/2018 |
| WO | WO 2019/005296 | 1/2019 |
| WO | WO 2019/070739 | 4/2019 |
| WO | WO 2019/113226 | 6/2019 |
| WO | WO 2019/246208 | 12/2019 |
| WO | WO 2020/117650 | 6/2020 |

OTHER PUBLICATIONS

Ingraham 1933 (The Bacteriostatic Action of Gentian Violet and its Dependence on the Oxidation-Reduction Potential; Journal of Bacteriology, vol. XXVI, No. 6. p. 573-598) (Year: 1933).*

Kotzian et al. 2007 (Oxides of platinum metal group as potential catalysts in carbonaceous amperometric biosensors based on oxidases; Sensors and Actuators B 124: 297-302). (Year: 2007).*

Berney et al. "A DNA diagnostic biosensor: development, characterization and performance" Sensors and Actuators B: Chemical: International Journal Devoted to Research and Development of Physical and Chemical Transducers, Elsevier BV, NL, vol. 68, No. 1-3, Aug. 25, 2000, pp. 100-108.

(56) References Cited

OTHER PUBLICATIONS

Dortet, Laurent et al., "Bloodstream Infections Caused by *Pseudomonas* spp.: How to Detect Carbapenemase Producers Directly from Blood Cultures", Journal of Clinical Microbiology, 52(4):1269-1273, Apr. 2014.
Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.
Dortet, Laurent et al., "Evaluation of the RAPIDECw Carba NP, the Rapid CARB Screenw and the Carba NP test for biochemical detection of carbapenemase-producing Enterobacteriaceae", J Antimicrob Chemother, 70:3014-3022, 2015.
Dortet, Laurent et al., "Further Proofs of Concept for the Carba NP Test", Antimicrobial Agents and Chemotherapy, 58(2):1269, Feb. 2014.
Dortet, Laurent et al., "Rapid Identification of Carbapenemase Types in Enterobacteriaceae and *Pseudomonas* spp. by Using a Biochemical Test", Antimicrobial Agents and Chemotherapy, 56(12):6437-6440, Dec. 2012.
Dutton 1978 (Redox potentiometry: Determination of midpoint potentials of oxidation-reduction components of biological electron-transfer systems; In Methods in Enzymology, 54:411-435) (Year: 1978).
Estrela, Pedro et al., "Label-Free Sub-picomolar Protein Detection with Field-Effect Transistors," Analytical Chemistry, vol. 82, No. 9, May 1, 2010, 3531-3536.
Grossi Marco et al. "Bacterial concentration detection using a portable embedded sensor system for environmental monitoring", 2017 7th IEE International Workshop on Advances in Senors and Interfaces (IWASI), IEEE, Jun. 15, 2017, pp. 246-251.
Hammock, Mallory L. et al., "Electronic readout ELISA with organic field-effect transistors as a prognostic test for preeclampsia," Advanced Materials, 26: 6138-6144. doi: 10.1002/adma.201401829.
Ivnitsky D et al: "Biosensors for Detection of Pathogenic Bacteria", Biosensors and Bioelectronics, Elsevier Science Ltd. UK, Amsterdam, NL, vol. 14, No. 7, Oct. 1, 1999, pp. 599-624.
J. Parce et al: "Detection of cell-affecting agents with a silicon biosensor", Science, vol. 246, No. 4927, Oct. 13, 1989 (Oct. 13, 1989), pp. 243-247.
Kang et al. "Survey of Redox-Active Moieties for Application in Multiplexed Electrochemical Biosensors", Anal. Chem., vol. 88, pp. 10452-10458, 2016.
Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).
Mathias, W. et al., "Selective Sodium Sensing with Gold-Coated Silicon Nanowire Field-Effect Transistors in a Differential Setup," ACS Nano 7, 5978-5983 (2013).
Nordmann, Patrice et al., "Strategies for identification of carbapenemase-producing Enterobacteriaceae", J Antimicrob Chemother, 68:487-489, 2013.

Oliu et al., "Impedimetric Sensors for Bacteria Detection," Biosensors—Micro and Nanoscale Applications, Chpt. 9 (Sep. 2015) p. 257-288.
Poghossian et al., "Penicillin Detection by Means of Field-Effect Based Sensors: EnFET, Capacitive EIS Sensor or LAPS?", *Sensors and Actuators B*, 78:237 (2001).
Poirel, Laurent et al., "Rapidec Carba NP Test for Rapid Detection of Carbapenemase Producers", Journal of Clinical Microbiology, 53(9):3003-3008, Sep. 2015.
Pourciel-Gouzy M L et al: "pH-ChemFET-based analysis devices for the bacterial activity monitoring." Sensors and Actuators B: Chemical: International Journal Devoted to Research and Development of Physical and Chemical Transducers, Elsevier BV, NL, vol. 134, No. Aug. 1, 28, 2008, pp. 339-344.
Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.
Schoning, Michael J., "Playing Around' with Field-Effect Sensors on the Basis of EIS Structures, LAPS and ISFETs," *Sensors*, 5:126-138 (2005).
Wan et al., 2011 (Impedimetric immunosensor doped with reduced graphene sheets fabricated by controllable electrodeposition for the non-labelled detection of bacteria; Biosensors and Bioelectronics 26 (2011) 1959-1964). (Year: 2011).
Yu Allen C et al: Moni tori ng bacterial growth using tunable resistive pulse sensing with a pore-based technique11 , Applied Microbiology and Biotechnology, Springer Berlin Heidelberg, Berlin/Heidelberg, vol. 98, No. 2, Nov. 29, 2013, pp. 855-862.
Zhang, Xuzhi et al.: Online Monitoring of Bacterial Growth with an Electrical Sensor11 , Analytical Chemistry, vol. 90, No. 10, Apr. 24, 2018 (Apr. 24, 2018), pp. 6006-6011.
Zhou, Yong-Jun et al.: Real-time Detection System for Amount of Bacteria Based on an Electrochemical Sensor, Instrument Technique and Sensor, vol. 2, No. 2, Feb. 28, 2014 (Feb. 28, 2014), pp. 71-72 and 86.
Zuhri et al. 2016 (Effect of Methylene Blue Addition as a Redox Mediator on Performance of Microbial Desalination Cell by Utilizing Tempe Wastewater; International Journal of Technology 6: 952-961). (Year: 2016).
"Minifor Laboratory Fermentor—Bioreactor", pp. 1-7, Feb. 24, 2017, Retrieved from the Internet: https://www.fermenter.net/pdf/LAMBDA_MINIFOR_laboratory_fermentor_description.pdf.
Jiang et al. "A User-Friendly Robotic Sample Preparation Program for Fully Automated Biological Sample Pipetting and Dilution to Benefit the Regulated Bioanalysis", Journal of Laboratory Automation, 2012, vol. 17, No. 3, pp. 211-221. (Year: 2012).
Kazuo Iwata, Akira Matsuda, Effect of Mixed Culture of Redox Potentials of Candida and Various Bacteria, Sep. 1962, Fungus and Fungus Disease, vol. 3, No. 2, pp. 56-60 [TMI comments: English counterpart is not available].
Rael et al. "Plasma Oxidation-Reduction Potential and Protein Oxidation in Traumatic Brain Injury", Journal of Neurotrauma, 2009, vol. 26, No. 8, pp. 1203-1211. (Year: 2009).

\* cited by examiner

APPARATUS, SYSTEMS, AND METHODS FOR DETERMINING SUSCEPTIBILITY OF MICROORGANISMS TO ANTI-INFECTIVES

CROSS-REFERENCE TO RELATED APPLICATIONS

This application is a continuation of U.S. patent application Ser. No. 16/716,945 filed on Dec. 17, 2019 which is a continuation of PCT Application No. PCT/US2018/031418 filed on May 7, 2018, which claims priority to U.S. Provisional Patent Application No. 62/525,671 filed Jun. 27, 2017, the contents of which are incorporated herein by reference in their entireties.

TECHNICAL FIELD

The present disclosure relates generally to in vitro detection of microorganisms or infectious agents and, more specifically, to apparatus, systems, and methods for determining the susceptibility of such microorganisms or infectious agents to anti-infectives.

BACKGROUND

Infections caused by anti-infective resistant microorganisms or infectious agents are a significant problem for healthcare professionals in hospitals, nursing homes, and other healthcare environments. Rapid detection of such microorganisms is crucial in order to prevent the spread of their resistance profiles. When faced with such an infection, a preferred course of action is for a clinician to use anti-infective compounds judiciously, preferably only those necessary to alleviate the infection. However, what occurs most frequently today is that broad spectrum anti-infectives are given to the patient to ensure adequacy of treatment. This tends to result in microorganisms with multiple anti-infective resistances. Ideally, the sensitivity of the microorganism to anti-infectives would be detected soon after its presence is identified.

Existing methods and instruments used to detect anti-infective resistance in microorganisms include costly and labor intensive microbial culturing techniques to isolate the microorganism and include tests such as agar disk diffusion or broth microdilution where anti-infectives are introduced as liquid suspensions, paper disks, or dried gradients on agar media. However, those methods require manual interpretation by skilled personnel and are prone to technical or clinician error.

While automated inspection of such panels or media can reduce the likelihood of clinician error, current instruments used to conduct these inspections are often complex and require the addition of reporter molecules or use of costly components such as transparent indium tin oxide (ITO) electrodes. In addition, current instruments often rely on an optical read-out of the investigated samples, which require bulky detection equipment.

As a result of the above limitations and restrictions, there is a need for improved apparatus, systems, and methods to quickly and effectively detect anti-infective resistant microorganisms in a patient sample.

SUMMARY

Various apparatus, systems and methods for detecting the susceptibility of an infectious agent in a sample to one or more anti-infectives are described herein. In one embodiment, a method of detecting a susceptibility of an infectious agent to an anti-infective comprises introducing a sample comprising an infectious agent to a first filter comprising a first filter surface and a second filter comprising a second filter surface. The first filter surface and the second filter surface can be configured to capture the infectious agent in the sample. The method can also involve introducing a first solution to the first filter surface such that the first solution is in fluid communication with the infectious agent captured on the first filter surface. The first solution can comprise a nutrient solution and an anti-infective. The method can further involve introducing a second solution to the second filter surface such that the second solution is in fluid communication with the infectious agent captured on the second filter surface. The second solution can comprise the nutrient solution but not comprise the anti-infective.

The method can also involve separating the first solution from the first filter surface such that at least a portion of the first solution previously in fluid communication with the first filter surface is delivered to a first sensor comprising a redox-active material. The method can also involve separating the second solution from the second filter surface such that at least a portion of the second solution previously in fluid communication with the second filter surface is delivered to a second sensor comprising the redox-active material. In alternative embodiments, the method can involve introducing the first solution directly to the first sensor comprising the redox-active material without introducing the first solution to the first filter surface. In these and other embodiments, the method can also involve introducing the second solution directly to the second sensor comprising the redox-active material without introducing the second solution to the second filter surface.

The method can further involve monitoring a first oxidation reduction potential (ORP) of the first solution previously in fluid communication with the first filter surface using at least one parameter analyzer coupled to the first sensor. The first ORP can be monitored in the absence of any added or exogenous reporter molecules in the first solution. The method can also involve monitoring a second ORP of the portion of the second solution previously in fluid communication with the second filter surface using the parameter analyzer coupled to the second sensor. The second ORP can be monitored in the absence of any added or exogenous reporter molecules in the second solution. The method can further involve comparing the first ORP with the second ORP to assess the susceptibility of the infectious agent to the anti-infective.

In another embodiment, a method of detecting a susceptibility of an infectious agent to an anti-infective comprises introducing a sample comprising an infectious agent to a first filter comprising a first filter surface and a second filter comprising a second filter surface. The first filter surface and the second filter surface can be configured to capture the infectious agent in the sample. The method can also involve introducing a first solution to the first filter surface such that the first solution is in fluid communication with the infectious agent captured on the first filter surface. The first solution can comprise a nutrient solution and an anti-infective. The method can also involve introducing a second solution to the second filter surface such that the second solution is in fluid communication with the infectious agent captured on the second filter surface. The second solution can comprise the nutrient solution but not comprise the anti-infective.

The method can further involve monitoring a first ORP of the first solution over time using at least one parameter analyzer coupled to a first sensor exposed to the first solution. The first sensor can comprise a redox-active material and the first ORP can be monitored in the absence of any added or exogenous reporter molecules in the first solution. The method can further involve monitoring a second ORP of the second solution over time using the parameter analyzer coupled to a second sensor exposed to the second solution. The second sensor can comprise the redox-active material and the second ORP can be monitored in the absence of any added or exogenous reporter molecules in the second solution. The method can also involve comparing the first ORP with the second ORP to assess the susceptibility of the infectious agent to the anti-infective.

In one embodiment, a system to detect a susceptibility of an infectious agent to an anti-infective can comprise a first filter comprising a first filter surface. The first filter surface can be configured to capture an infectious agent in a sample. The system can also include a second filter comprising a second filter surface. The second filter surface can be configured to capture the infectious agent in the sample. The system can also comprise a first fluid delivery conduit configured to introduce a first solution to the first filter surface such that the first solution is in fluid communication with the infectious agent captured on the first filter surface. The first solution can comprise a nutrient solution and an anti-infective. The system can also comprise a second fluid delivery conduit configured to introduce a second solution to the second filter surface such that the second solution is in fluid communication with the infectious agent captured on the second filter surface. The second solution can comprise the nutrient solution but not comprise the anti-infective. The system can further comprise a first sensor comprising a redox-active material configured to receive a portion of the first solution previously in fluid communication with the first filter surface and a first separation valve configured to separate the first solution in fluid communication with the first sensor from the first solution in fluid communication with the first filter.

The system can also comprise a second sensor comprising the redox-active material configured to receive a portion of the second solution previously in fluid communication with the second filter surface and a second separation valve configured to separate the second solution in fluid communication with the second sensor from the second solution in fluid communication with the second filter. The system can further comprise at least one parameter analyzer coupled to the first sensor and the second sensor. The parameter analyzer can be configured to monitor a first ORP of the first solution in fluid communication with the first sensor and to monitor a second ORP of the second solution in fluid communication with the second sensor. The parameter analyzer or another device can be configured to compare the first ORP with the second ORP to assess the susceptibility of the infectious agent to the anti-infective.

In some embodiments, the first sensor can comprise an active electrode and a reference electrode. In these and other embodiments, the active electrode and the reference electrode can be the only electrodes of the first sensor. Moreover, in some embodiments, the second sensor can comprise an active electrode and a reference electrode. In these and other embodiments, the active electrode and the reference electrode can be the only electrodes of the second sensor. In other embodiments, the first sensor and the second sensor can use the same reference electrode.

In some embodiments, the redox-active material can comprise a gold layer, a platinum layer, a metal oxide layer, a carbon layer, or a combination thereof. In these and other embodiments, the metal oxide layer can comprise an iridium oxide layer, a ruthenium oxide layer, or a combination thereof.

The reference electrode can be coated by a polymeric coating. For example, the reference electrode can be coated by a polyvinyl chloride (PVC) coating, a perfluorosulfonate coating (e.g., Nafion™), or a combination thereof.

The sample can comprise a biological sample, a bodily fluid, a wound swab or sample, a rectal swab or sample, a bacterial culture derived therefrom, or a combination thereof. The bodily fluid comprises urine, blood, sputum, saliva, breast milk, spinal fluid, semen, vaginal secretions, cerebrospinal fluid, synovial fluid, pleural fluid, peritoneal fluid, pericardial fluid, amniotic fluid, or a combination thereof.

The infectious agent can comprise bacteria from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia,* or a combination thereof. In other embodiments, the infectious agent can be a fungus or mold.

In some embodiments, the anti-infective can comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, anti-fungals, or a combination or derivation thereof. The anti-fungals can comprise Amphotericin B, Flucytosine, Fluconazole, Ketoconazole, Itraconazole, Posaconazole, Ravuconazole, Voriconazole, or a combination thereof.

In another embodiment, a system to detect a susceptibility of an infectious agent to an anti-infective can comprise a first filter comprising a first filter surface. The first filter surface can be configured to capture an infectious agent in a sample. The system can also include a second filter comprising a second filter surface. The second filter surface can be configured to capture the infectious agent in the sample. The system can also comprise a first fluid delivery conduit configured to introduce a first solution to the first filter surface such that the first solution is in fluid communication with the infectious agent captured on the first filter surface. The first solution can comprise a nutrient solution and an anti-infective. The system can also comprise a second fluid delivery conduit configured to introduce a second solution to the second filter surface such that the second solution is in fluid communication with the infectious agent captured on the second filter surface. The second solution can comprise the nutrient solution but not comprise the anti-infective.

The system can further comprise a first sensor comprising a redox-active material configured to receive a portion of the first solution and a second sensor comprising the redox-active material configured to receive a portion of the second solution. The system can also comprise at least one parameter analyzer coupled to the first sensor and the second sensor. The parameter analyzer can be configured to monitor a first ORP of the first solution in fluid communication with the first sensor and to monitor a second ORP of the second solution in fluid communication with the second sensor. The parameter analyzer or another device can be further configured to compare the first ORP with the second ORP to assess the susceptibility of the infectious agent to the anti-infective.

Also disclosed is a method of detecting a susceptibility of an infectious agent to an anti-infective. The method can involve introducing a sample comprising an infectious agent to a filter comprising a filter surface. The filter surface can be configured to capture the infectious agent in the sample. The method can also involve introducing a solution to the filter surface such that the solution is in fluid communication with the infectious agent captured on the filter surface. The solution can comprise a nutrient solution and an anti-infective. The method can further involve separating the solution from the filter surface such that at least a portion of the solution previously in contact with the filter surface is delivered to a sensor comprising a redox-active material. The method can further involve monitoring an ORP of the solution previously in fluid communication with the filter surface using at least one parameter analyzer coupled to the sensor to assess the susceptibility of the infectious agent to the anti-infective. The ORP of the solution can be monitored in the absence of any added or exogenous reporter molecules in the solution.

Another method of detecting a susceptibility of an infectious agent to an anti-infective is also disclosed. The method can involve introducing a sample comprising an infectious agent to a filter comprising a filter surface. The filter surface can be configured to capture the infectious agent in the sample. The method can also involve introducing a solution to the filter surface such that the solution is in fluid communication with the infectious agent captured on the filter surface. The solution can comprise nutrients and an anti-infective. The method can further involve monitoring an ORP of the solution using a parameter analyzer coupled to a sensor currently in fluid communication with the solution. The sensor can comprise a redox-active material. The ORP of the solution can be monitored in the absence of any added or exogenous reporter molecules in the solution to assess the susceptibility of the infectious agent to the anti-infective.

A system to detect a susceptibility of an infectious agent to an anti-infective is also disclosed. In one embodiment, the system can comprise a filter comprising a filter surface. The filter surface can be configured to capture an infectious agent in a sample and a fluid delivery conduit configured to introduce a solution to the filter surface such that the solution is in fluid communication with the infectious agent captured on the filter surface. The solution can comprise nutrients and an anti-infective. The system can also comprise a sensor comprising a redox-active material configured to receive a portion of the solution previously in contact with the filter surface and a separation valve configured to separate the solution in fluid communication with the sensor from the solution in fluid communication with the filter surface. The system can also comprise at least one parameter analyzer coupled to the sensor. The parameter analyzer can be configured to monitor an ORP of the solution in fluid communication with the sensor. The ORP of the solution can be monitored in the absence of any added or exogenous reporter molecules in the solution to assess the susceptibility of the infectious agent to the anti-infective.

Another system to detect a susceptibility of an infectious agent to an anti-infective is also disclosed. In one embodiment, the system can comprise a filter comprising a filter surface. The filter surface can be configured to capture an infectious agent in a sample and a fluid delivery conduit configured to introduce a solution to the filter surface such that the solution is in fluid communication with the infectious agent captured on the filter surface. The solution can comprise a nutrient solution and an anti-infective. The system can also comprise a sensor comprising a redox-active material configured to receive a portion of the solution and a parameter analyzer coupled to the sensor. The parameter analyzer can be configured to monitor an ORP of the solution in fluid communication with the sensor. The ORP of the solution can be monitored in the absence of any added or exogenous reporter molecules in the solution to assess the susceptibility of the infectious agent to the anti-infective.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
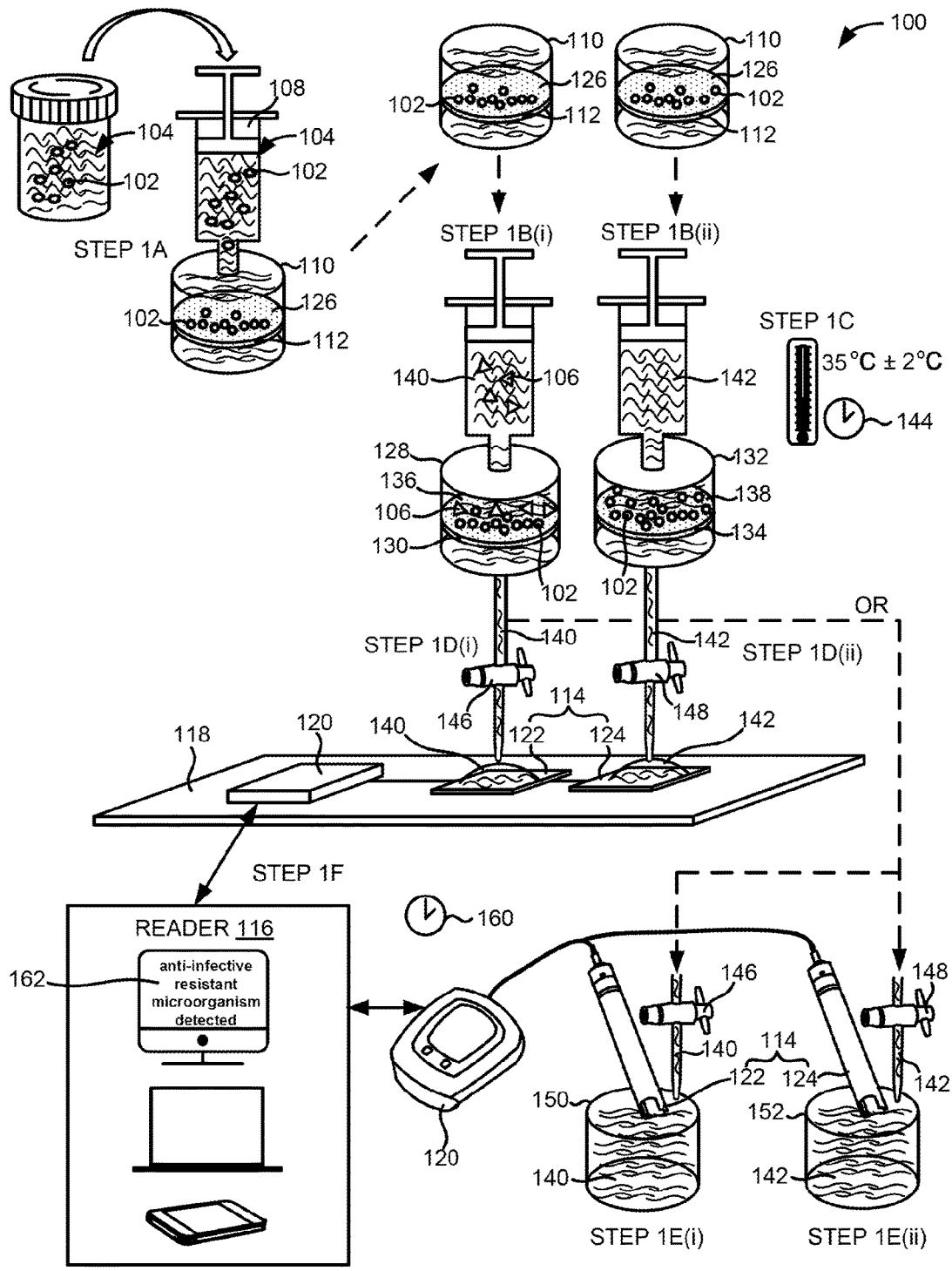
FIG. 1 illustrates one embodiment of a system for detecting a susceptibility of an infectious agent to one or more anti-infectives.

FIG. 1 illustrates an embodiment of a system 100 for detecting or assessing a susceptibility of an infectious agent 102 in a sample 104 to an anti-infective 106. The system 100 can comprise a plurality of fluid delivery conduits 108, a plurality of filter housings 110 each containing a filter 112, a plurality of sensors 114, and at least one reader 116.

As shown in the example embodiment of FIG. 1, the one or more sensors 114 can be disposed or located on a surface of a substrate 118. The substrate 118 can be comprised of a polymeric material, a metal, a ceramic, a semiconductor layer, an oxide layer, an insulator, or a combination thereof. The system 100 can also include at least one parameter analyzer 120 such as a voltmeter or a multimeter electrically coupled to the sensors 114. In one embodiment, the parameter analyzer 120 can be integrated into one device with the sensors 114. For example, the parameter analyzer 120 can be fabricated on the same substrate 118 as the sensors 114 or in a vicinity of the sensors 114. In another embodiment, the parameter analyzer 120 can be a standalone unit or device coupled to the sensors 114.

The sensors 114 can comprise at least a first sensor 122 and a second sensor 124. The sensors 114, including the first sensor 122 and the second sensor 124, will be discussed in more detail in the sections that follow.

The sample 104 can comprise at least one of a biological sample, a bodily fluid, a wound swab or sample, a rectal swab or sample, and a bacterial culture derived from the biological sample, the bodily fluid, the wound swab or sample, or the rectal swab or sample. The bodily fluid can comprise urine, blood, serum, plasma, saliva, sputum, semen, breast milk, joint fluid, spinal fluid, wound material, mucus, fluid accompanying stool, re-suspended rectal or wound swabs, vaginal secretions, cerebrospinal fluid, synovial fluid, pleural fluid, peritoneal fluid, pericardial fluid, amniotic fluid, or a combination thereof.

The infectious agent 102 can be any metabolizing single or multi-cellular organism including a bacteria or fungus. In certain embodiments, the infectious agent 102 can be one or more bacteria selected from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the infectious agent 102 can be one or more fungi selected from the genera *Candida* or *Cryptococcus* or mold.

The fluid delivery conduits 108 can include tubes, pumps, containers, or microfluidic channels for delivering buffers, reagents, fluid samples including the sample 104 or solubilized solutions thereof, other solutions, or a combination thereof to and between devices, apparatus, or containers in the system. For example, as shown in FIG. 1, the fluid delivery conduits 108 can refer to parts of a pump such as a syringe pump. In other embodiments, the fluid delivery conduits 108 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 108 can include or refer to at least part of an injection cartridge, a pipette, a reaction tube, a capillary, a test tube, or a combination thereof. The fluid delivery conduits 108 can also be part of a vacuum system configured to draw fluid to or through the filters 112 under vacuum. Moreover, the fluid delivery conduits 108 can include or refer to at least part of a multichannel delivery system or pipette.

The filter housing 110 can be a container or vessel configured to secure or enclose the filter 112. For example, the filter housing 110 can be a protective chamber, a microfluidic cartridge, or a combination thereof. The protective chamber can be an electrically isolated environment. The protective chamber can also be a temperature controlled chamber, a light controlled chamber, or a combination thereof.

The filter 112 can have a filter surface 126. The filter 112 can trap or isolate the infectious agent 102 by depositing or capturing the infectious agent 102 onto the filter surface 126. The filter surface 126 can be an external surface, an internal surface extending into the filter 112, or a combination thereof. The filter 112 can be made of, but is not limited to, cellulose acetate, regenerated cellulose, nylon, polystyrene, polyvinylidene fluoride (PVDF), polyethersulfone (PES), polytetrafluorethylene (PTFE), glass microfiber, or a combination thereof.

In one embodiment, the filter 112 can have filter pores sized between 0.1 μm and 0.5 μm. For example, the filter 112 can have filter pores sized at about 0.2 μm. In other embodiments, the filter 112 can have filter pores sized between 0.5 μm and 1.0 μm. In some embodiments, the filter 112 can have filter pores of sequentially smaller pore sizes along the depth of the filter 112. For example, the filter 112 can have larger filter pores at the top of the filter and progressively smaller filter pores toward the bottom of the filter. In another embodiment, the filter 112 can have filter pores of a similar pore size throughout the entire filter. In these embodiments, the filter surface 126 can refer to the surface of the pores or areas adjacent to the pores. In another embodiment, the filter 112 can be a mesh or matrix structure and the filter surface 126 can be a mesh or matrix surface. The filter 112 can be a non-clogging filter such as a high-capacity filter. Although not shown in FIG. 1, it is contemplated by this disclosure that the filter 112 can refer to a plurality of filters in a stacked arrangement.

The filter 112 can also be a multilayer filter. For example, the filter 112 can comprise a top layer or several upper layers made of graded density glass microfiber or polypropylene having filter pores sized between 1.0 μm and 5.0 μm and a lower layer or several lower layers made of nylon, glass microfiber, or PES having filter pores sized between 0.1 μm and 0.5 μm.

The filter 112 can capture and hold the infectious agent 102 when a sample 104 comprising or carrying the infectious agent 102 is introduced to the filter 112 in step 1A shown in FIG. 1. For example, the sample 104 can be introduced to the filter 112 when the sample 104 is poured over the filter 112 or injected through the filter 112. The filter 112 can isolate or separate the infectious agent 102 or other molecules or cells from the rest of the sample 104.

As illustrated in FIG. 1, the fluid delivery conduit 108 can deliver or inject the sample 104 into the filter housing 110 in step 1A. In another embodiment not shown in FIG. 1, a stimulus solution can be added to the sample 104 before introducing the sample 104 to the filter 112. The stimulus solution can be a nutrient or growth solution.

In an alternative embodiment not shown in FIG. 1, the sample 104 can be pre-filtered before step 1A. This pre-filtering step can involve filtering the sample 104 using another instance of a filter, a microfluidic filter, or a combination thereof to filter out debris, inorganic material, and larger cellular components including blood cells or epithelial cells from the sample 104.

Although FIG. 1 shows the fluid delivery conduit 108 delivering or injecting the sample 104 into one instance of the filter housing 110 containing the filter 112 in step 1A, it should be understood by one of ordinary skill in the art that the fluid delivery conduit 108 can deliver or inject the sample 104 into multiple instances of the filter housing 110 with each filter housing 110 containing its own filter 112. For example, the fluid delivery conduit 108 can deliver, inject, or otherwise introduce the sample 104 comprising the infectious agent 102 to a first filter housing 128 comprising a first filter 130 and a second filter housing 132 comprising a second filter 134. The first filter 130 and the second filter 134 can refer to different instances of the same filter 112. The first filter 130 can have a first filter surface 136 configured to capture and trap the infectious agent 102 in the sample 104. In addition, the second filter 134 can also have a second filter surface 138 configured to capture and trap the infectious agent 102 in the sample 104.

The same fluid delivery conduit 108 or another fluid delivery conduit can be used to deliver or inject a first solution 140 to the first filter housing 128 in step 1B(i). In addition, the same fluid delivery conduit 108 or another fluid delivery conduit can be used to deliver or inject a second solution 142 to the second filter housing 132 in step 1B(ii). The first solution 140 can comprise a nutrient solution and at least one anti-infective 106. The second solution 142 can be a nutrient solution without any anti-infectives 106. In one embodiment, the nutrient solution delivered or injected in step 1(B)(ii) can be the same as the nutrient solution delivered or injected in step 1(B)(i).

In one embodiment, the nutrient solution can be a solution containing bacto-tryptone, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose, or a combination thereof. In another embodiment the nutrient solution can include a growth inducer. The growth inducer can comprise a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the nutrient solution can comprise Tryptone, yeast extract, sodium chloride, and glucose. The nutrient solution can be used to counteract the buffering effects of ions or substances present in the sample 104 when the sample 104 is composed of a bodily fluid.

The anti-infective 106 can comprise a bacteriostatic anti-infective, a bactericidal anti-infective, an anti-fungal anti-infective, or a combination thereof. In certain embodiments, the bacteriostatic anti-infective can comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, anti-fungals, or a combination or derivation thereof. The anti-fungals can comprise Amphotericin B, Flucytosine, Fluconazole, Ketoconazole, Itraconazole, Posaconazole, Ravuconazole, Voriconazole, or a combination thereof.

In some embodiments, a bacterial growth inhibitor or stimulator can also be added to the nutrient solution. The bacterial growth inhibitor or stimulator can selectively inhibit or promote the growth of gram positive or gram negative bacteria. The bacterial growth inhibitor can comprise a dye or a chemical compound or reagent. In some embodiments, the dye can include, but is not limited to, methylene blue, bromothymol blue, Eosin B, Safranin O, Crystal violet, colistin, nalidixic acid, yeast extract peptone dextrose (YEPD), bismuth ammonium citrate, sodium sulfite, or a combination thereof. The chemical compound or reagent can include, but is not limited to, sodium azide, bile salts, sodium chloride, tetrathionate, or a combination thereof.

The first filter 130 and the second filter 134 can then be heated to a temperature of between 30° C. and 40° C. (e.g., 35° C.±2° C.) and allowed to incubate for an incubation period 144 in step 1C. The incubation period 144 can range from 15 minutes to over one hour. In other embodiments, the incubation period 144 can be less than 15 minutes or up to 48 hours.

The incubation period 144 can be adjusted based on the type of infectious agent 102 suspected in the sample 104, such as the type of bacteria or fungus. The incubation period 144 can also be adjusted based on the type of anti-infective 106, the mechanism of action of the anti-infective 106, the amount of the sample 104, or a combination thereof. The incubation period 144 can also be start-delayed or a pre-incubation time period can be added before the start of the incubation period 144. The start-delay or the pre-incubation time period can be added for slower acting drugs or anti-infectives 106 (e.g., β-lactams). In some embodiments, the start-delay or the pre-incubation time period can be between 10 minutes and 2 hours. In other embodiments, the start-delay or the pre-incubation time period can be as long as needed for the drug or anti-infective 106 to take effect. During the start-delay or pre-incubation time period, readings or measurements from the first sensor 122, the second sensor 124, or a combination thereof would not be used or would not be included as part of any growth curves generated. The start-delay or the pre-incubation time period is particularly useful for instances where higher inoculums or a higher concentration of infectious agents 102 is present in the sample 104 or isolated on the filters 112 and where the signal is generated quite fast in comparison to the mode of action of the drug or anti-infective 106.

In one embodiment, the first filter 130 and the second filter 134 can be incubated while in their respective filter housings. In another embodiment, the first filter 130 and the second filter 134 can be removed from their respective filter housings prior to incubation. In some embodiments, the first filter 130 comprising the infectious agent 102 can be incubated while in fluid communication with the first solution 140. In these embodiments, the second filter 134 comprising the infectious agent 102 can be incubated while in fluid communication with the second solution 142. Benefits of incubating the first filter 130, the second filter 134, or a combination thereof include speeding up the kinetics of the mechanism of action of the anti-infective 106, providing the infectious agent 102 time to grow, or a combination thereof.

After or while incubating the first filter 130 in step 1C, at least a portion of the first solution 140 previously in fluid communication with the first filter surface 136 can be separated from the first filter surface 136. For example, the first filter housing 128 can comprise an opening, channel, or outlet for evacuating or siphoning the first solution 140 previously in fluid communication with the first filter surface 136 from the first filter housing 128. The portion of the first solution 140 separated from the first filter surface 136 can then be directed or introduced to an instance of the first sensor 122 fabricated or located on a substrate 118 in step 1D(i). As shown in FIG. 1, the first sensor 122 can be fabricated or located on the same substrate 118 as the second sensor 124. For example, the first sensor 122 and the second sensor 124 can both be sensors on one test strip, integrated circuit, or micro-electro-mechanical system (MEMS) device. Moreover, in some embodiments, at least a part of the parameter analyzer 120 can also be integrated with the substrate 118.

The system 100 can also comprise a first separation valve 146 configured to separate the portion of the first solution 140 in fluid communication with the first sensor 122 from the portion of the first solution 140 still in fluid communication with the first filter surface 136. In one embodiment, the first separation valve 146 can comprise or be a two-way or three-way stopcock valve, a pinch valve, a push button valve, a needle valve, a microfluidic valve, or a combination thereof. In some variations, a stopper, a barrier, cap, a plug of air, or a combination thereof can be used in lieu of or in addition to the first separation valve 146. When a plug of air is used in lieu of the first separation valve 146, certain components of the system 100 can be agitated.

Similarly, after or while incubating the second filter 134 in step 1C, at least a portion of the second solution 140 previously in fluid communication with the second filter surface 138 can be separated from the second filter surface 138. For example, the second filter housing 132 can comprise an opening, channel, or outlet for evacuating or siphoning the second solution 142 previously in fluid communication with the second filter surface 138 from the second filter housing 132. The portion of the second solution 142 separated from the second filter surface 138 can then be directed or introduced to an instance of the second sensor 124 fabricated or located on a substrate 118 in step 1D(ii). As shown in FIG. 1, the second sensor 124 can be fabricated or located on the same substrate 118 as the second sensor 124. For example, the first sensor 122 and the second sensor 124 can both be sensors on one test strip, integrated circuit, or micro-electro-mechanical system (MEMS) device. Moreover, in some embodiments, at least a part of the parameter analyzer 120 can also be integrated with the substrate 118.

In addition, the system 100 can comprise a second separation valve 148 configured to separate the portion of the second solution 142 in fluid communication with the second sensor 124 from the portion of the second solution 142 still in fluid communication with the second filter surface 138. In one embodiment, the second separation valve 148 can comprise or be a two-way or three-way stopcock valve, a pinch valve, a push button valve, a needle valve, a microfluidic valve, or a combination thereof. In some variations, a stopper, a barrier, a cap, a plug of air, or a combination thereof can be used in lieu of or in addition to the second separation valve 148. When a plug of air is used in lieu of the second separation valve 148, certain components of the system 100 can be agitated.

While FIG. 1 illustrates only two sensors 114 (the first sensor 122 and the second sensor 124) on the substrate 118 being used to analyze solutions previously in contact with the infectious agents 102, it is contemplated by this disclosure that the substrate 118 can accommodate any number of sensors 114. For example, the substrate 118 can be a support or housing for a high throughput assay plate or well plate such as a 96 well plate, a 192 well plate, or a 384 well plate. In this example, each of the wells of the well plate can comprise or be in fluid communication with one or more sensors 114.

At least one parameter analyzer 120 coupled to the first sensor 122 can monitor an ORP of the first solution 140 in fluid communication with the first sensor 122. The ORP of the first solution 140 can be referred to as the first ORP. In addition, the same parameter analyzer 120 or another parameter analyzer coupled to the second sensor 124 can monitor an ORP of the second solution 142. The ORP of the second solution 142 can be referred to as the second ORP. The first ORP and the second ORP can be monitored in the absence of any added or exogenous reporter molecules in either the first solution 140 or the second solution 142 to assess the susceptibility of the infectious agent 102 to the anti-infective 106.

Alternatively, FIG. 1 also illustrates that a portion of the first solution 140 separated from the first filter surface 136 can be directed or introduced to a first measurement container 150 in step 1E(i). The first measurement container 150 can be a separate container or housing than the first filter housing 128. The first solution 140 can then be monitored by directly immersing at least part of a handheld or probe instance of the first sensor 122 into the first solution 140. For example, the handheld or probe instance of the first sensor 122 can be an ORP sensor coupled to a standalone parameter analyzer 120 such as a voltmeter or multimeter.

Moreover, a portion of the second solution 142 separated from the second filter surface 138 can also be directed or introduced to a second measurement container 152 in step 1E(ii). The second measurement container 152 can be a separate container or housing than the second filter housing 132. The second solution 142 can then be monitored by directly immersing at least part of a handheld or probe instance of the second sensor 124 into the second solution 142. For example, the handheld or probe instance of the second sensor 124 can be an ORP sensor coupled to a standalone parameter analyzer 120 such as a voltmeter or multimeter.

The first solution 140 and the second solution 142 can each have a solution characteristic. The solution characteristics of the first solution 140 and the second solution 142 can change as the amount of electro-active redox species changes due to the energy use, oxygen uptake or release, growth, or metabolism of the infectious agents 102 isolated or trapped by the filters 112. For example, the amount of electro-active redox species in the first solution 140 can change as a result of cellular activity (e.g., microbial aerobic or anaerobic respiration) undertaken by the infectious agents 102 captured by the first filter 130. Also, for example, the amount of electro-active redox species in the second solution 142 can change as a result of cellular activity (e.g., microbial aerobic or anaerobic respiration) undertaken by the infectious agents 102 captured by the second filter 134. As a more specific example, the amount of electron donors from Table 1 (e.g., the amount of energy carriers such as nicotinamide adenine dinucleotide (NADH) and flavin adenine dinucleotide ($FADH_2$)) in the first solution 140 or the second solution 142 can change due to the growth or lack thereof of the infectious agents 102 captured by the first filter 130 or the second filter 134. Also, as another more specific example, the amount of oxygen depleted in the first solution 140 or the second solution 142 due to aerobic respiration can change due to the growth or lack thereof of the infectious agents 102 captured by the first filter 130 or the second filter 134.

In one embodiment, the parameter analyzer 120 or the reader 116 can comprise a controller or processors to execute logical commands concerning the comparison of the first ORP with the second ORP and to generate a read-out or signal concerning a result of the comparison or detection.

For example, the parameter analyzer 120 or the reader 116 can determine or assess the susceptibility of the infectious agent 102 in the sample 104 as resistant to the anti-infective 106 when the parameter analyzer 120 or the reader 116 fails to detect certain statistically significant differences between the first ORP and the second ORP. This statistically significant difference can be a difference exceeding a threshold value. Conversely, the parameter analyzer 120 or the reader 116 can determine or assess the susceptibility of the infectious agent 102 as not resistant to the anti-infective 106

TABLE 1

Below is a "redox tower" visualizing potential electron donors and acceptors which can be utilized by microorganisms or infectious agents during the course of metabolism. An electron donor will have a greater negative potential than the electron acceptor. In aerobic respiration for example, $O_2$ can serve as a terminal electron acceptor whereas in anaerobic respiration, the terminal electron acceptor can comprise $NO_3^-$, $Fe^{3+}$, $Mn^{4+}$, $SO_4^{2-}$, or $CO_2$.

| Electron Donor and Acceptor Pairs | Measured Standard Reduction Potential $E'_0$ (mV) | Standard Reduction Potential $E'_0$ (mV) range |
|---|---|---|
| Glucose ⇌ 2 Pyruvate + $2e^-$ | −720 | −700 |
| | | −600 |
| Glucose ⇌ 6 $CO_2$ + $24e^-$ | −500 | −500 |
| $H_2$ ⇌ $2H^+$ + $2e^-$ | −420 | −400 |
| NADH ⇌ $NAD^+$ + $2e^-$ | −320 | −300 |
| 2 GSH ⇌ GSSG + $2e^-$ | −240 | −200 |
| $H_2S$ ⇌ $SO_4^{2-}$ + $8e^-$ | −220 | |
| $FADH_2$ ⇌ FAD + $2H^+$ + $2e^-$ | −220 | |
| Lactate ⇌ Pyruvate + $2e^-$ | −190 | −100 |
| Succinate ⇌ Fumarate + $2e^-$ | 33 | 0 |
| Cyt b (red) ⇌ Cyt b (ox) + $e^-$ | 80 | |
| Ubiquinol ⇌ Ubiquinone + $2e^-$ | 110 | 100 |
| Cyt c (red) ⇌ Cyt c (ox) + $e^-$ | 250 | 200 |
| Cyt a (red) ⇌ Cyt a (ox) + $e^-$ | 290 | |
| | | 300 |
| $NO_2^-$ + $H_2O$ ⇌ $NO_3^-$ + $2e^-$ | 420 | 400 |
| $NH_4^+$ + $H_2O$ ⇌ $NO_2^-$ + $6e^-$ | 440 | |
| $Mn^{2+}$ + $H_2O$ ⇌ $MnO_2$ + $2e^-$ | 460 | |
| | | 500 |
| | | 600 |
| ½ $N_2$ + $3H_2O$ ⇌ $NO_3^-$ + $5e^-$ | 740 | 700 |
| $Fe^{2+}$ ⇌ $Fe^{3+}$ + $1e^-$ | 770 | |
| $H_2O$ ⇌ ½ $O_2$ + $2H^+$ + $2e^-$ | 820 | 800 |
| | | 900 |

The parameter analyzer 120 or another device, such as the reader 116, coupled to the parameter analyzer 120 can be configured to compare the first ORP with the second ORP to assess the susceptibility of the infectious agent 102 in the sample 104 to the anti-infective 106 in step 1F. The parameter analyzer 120 or the reader 116 can compare the first ORP with the second ORP over a period of time. The period of time can be referred to as a detection window 160. The parameter analyzer 120 or the reader 116 can assess the susceptibility of the infectious agent 102 to the anti-infective 106 within the detection window 160. In one embodiment, the detection window 160 can be between 60 minutes and 120 minutes. In other embodiments, the detection window 160 can be between 5 minutes and 60 minutes. In additional embodiments, the detection window 160 can be greater than 120 minutes.

when the parameter analyzer 120 or the reader 116 detects certain statistically significant differences between the first ORP and the second ORP within the detection window 160.

In other embodiments, the parameter analyzer 120 or the reader 116 can assess the level of susceptibility of the infectious agent 102 in the sample 104 on a tiered scale. For example, the parameter analyzer 120 or the reader 116 can assess the susceptibility of the infectious agent 102 in the sample 104 as being resistant, of intermediate susceptibility, or susceptible to the anti-infective 106. In these embodiments, several first filter housings 128 can each comprise a different concentration of the anti-infective 106 to assess the level of susceptibility of the infectious agent 102 to the anti-infective 106.

The parameter analyzer 120 can also be connected to or communicatively coupled to a device having a display 162 or a display component configured to provide a result of the detection or a read-out of the electrical characteristic of the sensors 114. In certain embodiments, the reader 116 can be a mobile device, a handheld device, a tablet device, or a computing device such as a laptop or desktop computer and the display 162 can be a mobile device display, a handheld device display, a tablet display, or a laptop or desktop monitor. In some embodiments, the parameter analyzer 120 can wirelessly communicate a signal or result to the reader 116 or another computing device having the display 162.

The steps depicted in FIG. 1 do not require the particular order shown to achieve the desired result. Moreover, certain steps or processes may be omitted or occur in parallel in order to achieve the desired result.

Figure 2:
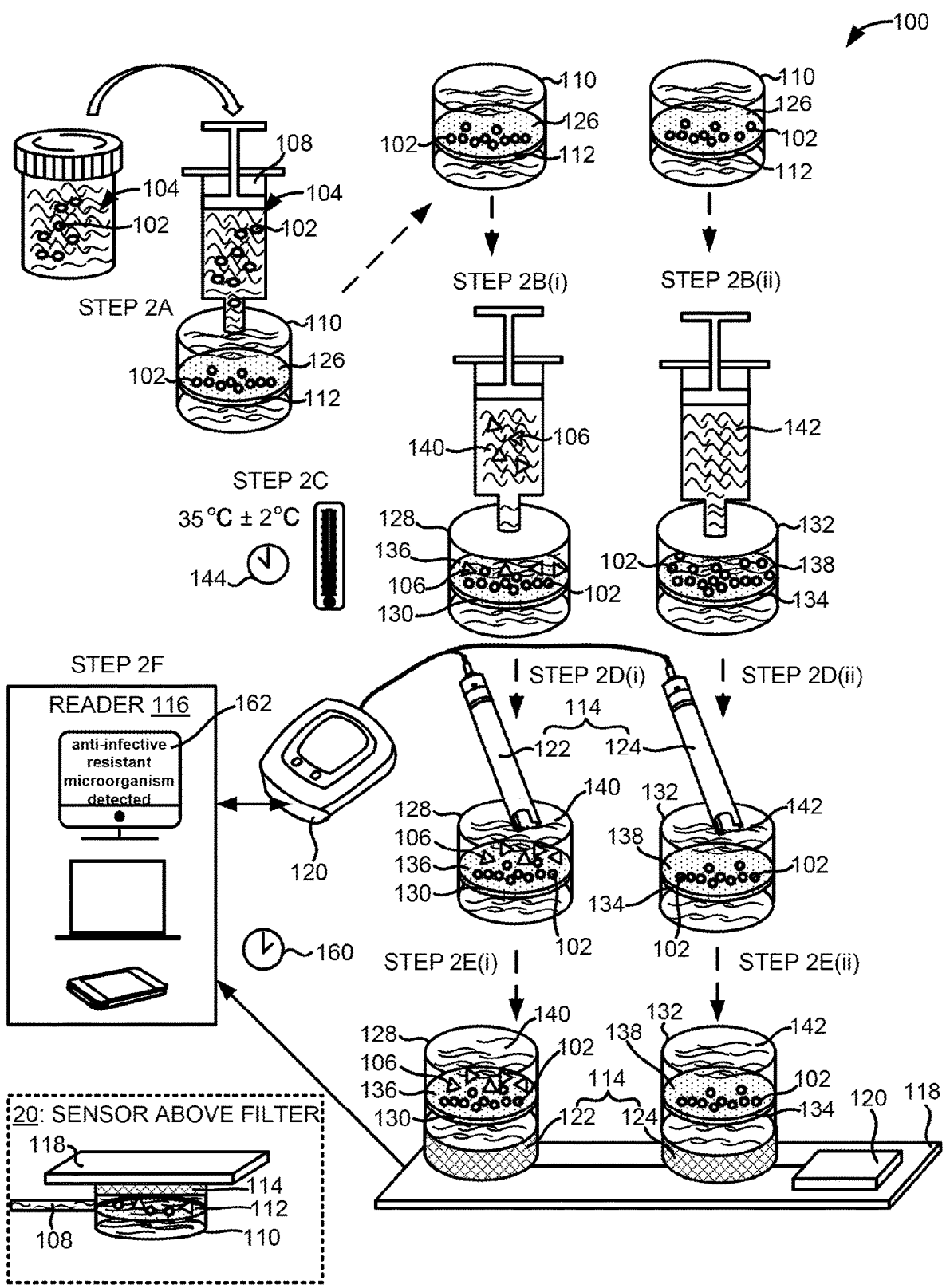
FIG. 2 illustrates another embodiment of a system for detecting a susceptibility of an infectious agent to one or more anti-infectives.

FIG. 2 illustrates another embodiment of the system 100 for detecting or assessing the susceptibility of an infectious agent 102 to an anti-infective 106. The system 100 shown in FIG. 2 can comprise the same fluid delivery conduits 108, sensors 114 including the first sensor 122 and the second sensor 124, filter housings 110 including the first filter housing 128 and the second filter housing 132, filters 112 including the first filter 130 and the second filter 134, readers 116, and parameter analyzers 120 as those shown in FIG. 1.

As illustrated in FIG. 2, the fluid delivery conduit 108 can deliver or inject the sample 104 into the filter housing 110 in step 2A. In another embodiment not shown in FIG. 2, a stimulus solution can be added to the sample 104 before introducing the sample 104 to the filter 112. The stimulus solution can comprise a nutrient solution or growth solution.

In an alternative embodiment not shown in FIG. 2, the sample 104 can be pre-filtered before step 2A. This pre-filtering step can involve filtering the sample 104 using another instance of a filter, a microfluidic filter, or a combination thereof to filter out debris, inorganic material, and larger cellular components including blood cells or epithelial cells from the sample 104.

Although FIG. 2 shows the fluid delivery conduit 108 delivering or injecting the sample 104 into one instance of the filter housing 110 containing the filter 112 in step 2A, it should be understood by one of ordinary skill in the art that the fluid delivery conduit 108 can deliver or inject the sample 104 into multiple instances of the filter housing 110 with each filter housing 110 containing its own filter 112. For example, the fluid delivery conduit 108 can deliver, inject, or otherwise introduce the sample 104 comprising the infectious agent 102 to a first filter housing 128 comprising a first filter 130 and a second filter housing 132 comprising a second filter 134. The first filter 130 and the second filter 134 can refer to different instances of the same filter 112. The first filter 130 can have a first filter surface 136 configured to capture and trap the infectious agent 102 in the sample 104. In addition, the second filter 134 can also have a second filter surface 138 configured to capture and trap the infectious agent 102 in the sample 104.

The same fluid delivery conduit 108 or another fluid delivery conduit can be used to deliver or inject a first solution 140 to the first filter housing 128 in step 2B(i). In addition, the same fluid delivery conduit 108 or another fluid delivery conduit can be used to deliver or inject a second solution 142 to the second filter housing 132 in step 2B(ii). The first solution 140 can comprise a nutrient solution and at least one anti-infective 106. The second solution 142 can be a nutrient solution without any anti-infectives 106. In one embodiment, the nutrient solution delivered or injected in step 2(B)(ii) can be the same as the nutrient solution delivered or injected in step 2(B)(i).

The nutrient solution can be a solution containing bacto-tryptone, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose, or a combination thereof. In another embodiment, the nutrient solution can include a growth inducer. The growth inducer can comprise a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the nutrient solution can comprise Tryptone, yeast extract, sodium chloride, and glucose. The nutrient solution can be used to counteract the buffering effects of ions or substances present in the sample 104 when the sample 104 is composed of a bodily fluid.

The anti-infective 106 can comprise a bacteriostatic anti-infective, a bactericidal anti-infective, an anti-fungal anti-infective, or a combination thereof. In certain embodiments, the bacteriostatic anti-infective can comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, anti-fungals, or a combination or derivation thereof. The anti-fungals can comprise Amphotericin B, Flucytosine, Fluconazole, Ketoconazole, Itraconazole, Posaconazole, Ravuconazole, Voriconazole, or a combination thereof.

In some embodiments, a bacterial growth inhibitor can also be added to the nutrient solution. The bacterial growth inhibitor can selectively inhibit or promote the growth of gram positive or gram negative bacteria. The bacterial growth inhibitor can comprise a dye or a chemical compound or reagent. In some embodiments, the dye can include, but is not limited to, methylene blue, bromothymol blue, Eosin B, Safranin O, Crystal violet, colistin, nalidixic acid, yeast extract peptone dextrose (YEPD), bismuth ammonium citrate, sodium sulfite, or a combination thereof. The chemical compound or reagent can include, but is not limited to, sodium azide, bile salts, sodium chloride, tetrathionate, or a combination thereof.

The first filter 130 and the second filter 134 can then be heated to a temperature of between 30° C. and 40° C. (e.g., 35° C.±2° C.) and allowed to incubate for an incubation period 144 in step 2C. The incubation period 144 can range from 15 minutes to over one hour. In other embodiments, the incubation period 144 can be less than 15 minutes or up to 48 hours.

The incubation period 144 can be adjusted based on the type of infectious agent 102 suspected in the sample 104, such as the type of bacteria or fungus. The incubation period 144 can also be adjusted based on the type of anti-infective 106, the mechanism of action of the anti-infective 106, the amount of the sample 104, or a combination thereof. The incubation period 144 can also be start-delayed or a pre-incubation time period can be added before the start of the incubation period 144. The start-delay or the pre-incubation time period can be added for slower-acting drugs or anti-infectives 106 (e.g., β-lactams). In some embodiments, the start-delay or the pre-incubation time period can be between 10 minutes and 2 hours. In other embodiments, the start-delay or the pre-incubation time period can be as long as needed for the drug or anti-infective 106 to take effect. During the start-delay or pre-incubation time period, readings or measurements from the first sensor 122, the second sensor 124, or a combination thereof would not be used or would not be included as part of any growth curves generated. The start-delay or the pre-incubation time period is particularly useful for instances where higher inoculums or a higher concentration of infectious agents 102 is present in the sample 104 or isolated on the filters 112 and where the signal is generated quite fast in comparison to the mode of action of the drug or anti-infective 106.

In one embodiment, the first filter 130 and the second filter 134 can be incubated while in their respective filter housings. In another embodiment, the first filter 130 and the second filter 134 can be removed from their respective filter housings prior to incubation. In some embodiments, the first filter 130 comprising the infectious agent 102 can be incubated while in fluid communication with the first solution 140. In these embodiments, the second filter 134 comprising the infectious agent 102 can be incubated while in fluid communication with the second solution 142. Benefits of incubating the first filter 130, the second filter 134, or a combination thereof include speeding up the kinetics of the mechanism of action of the anti-infective 106, providing the infectious agent 102 time to grow, or a combination thereof.

After or while incubating the first filter 130 in step 2C, the first solution 140 within the first filter housing 128 or the first solution 140 in fluid communication with the first filter surface 136 can be monitored by directly immersing at least part of a handheld or probe instance of the first sensor 122 into the first solution 140 in step 2D(i). For example, the handheld or probe instance of the first sensor 122 can be an ORP sensor coupled to a standalone parameter analyzer 120 such as a voltmeter or multimeter.

Similarly, after or while incubating the second filter 134 in step 2C, the second solution 142 within the second filter housing 132 or the second solution 142 in fluid communication with the second filter surface 138 can be monitored by directly immersing at least part of a handheld or probe instance of the second sensor 124 into the second solution 142. For example, the handheld or probe instance of the second sensor 124 can be an ORP sensor coupled to a standalone parameter analyzer 120 such as a voltmeter or multimeter.

Alternatively, as shown in FIG. 2, the first filter housing 128, the second filter housing 132, or a combination thereof can be directly coupled to or fabricated on a substrate 118 comprising sensors 114. For example, the first sensor 122 and the second sensor 124 can both be sensors on a test strip, an integrated circuit, or a micro-electro-mechanical system (MEMS) device. Moreover, in some embodiments, at least a part of the parameter analyzer 120 can also be integrated with the substrate 118. In this embodiment, the first solution 140 can be monitored by the first sensor 122 coupled to or fabricated on the substrate 118 as soon as the first solution 140 is delivered, injected, or otherwise introduced to the first filter housing 128 in step 2E(i). Also, in this embodiment, the second solution 142 can be monitored by the second sensor 124 coupled to or fabricated on the substrate 118 as soon as the second solution 142 is delivered, injected, or otherwise introduced to the second filter housing 132 in step 2E(ii).

While FIG. 2 illustrates only two sensors 114 (the first sensor 122 and the second sensor 124) on the substrate 118 being used to analyze solutions previously in contact with the infectious agents 102, it is contemplated by this disclosure that the substrate 118 can accommodate any number of sensors 114. For example, the substrate 118 can be a support or housing for a high throughput assay plate or well plate such as a 96 well plate, a 192 well plate, or a 384 well plate. In this example, each of the wells of the well plate can comprise or be in fluid communication with one or more sensors 114.

Moreover, inset 20 illustrates an alternative embodiment where the sensor 114 (e.g., any of the first sensor 122 or the second sensor 124) is positioned vertically above the filter housing 110 (e.g., any of the first filter housing 128 or the second filter housing 132) comprising the filter 112 (e.g., any of the first filter 130 or the second filter 134). In this embodiment, the fluid delivery conduit 108 can deliver, inject, pump, or otherwise introduce the sample 104, a solution carrying the sample 104, or any other solutions into the interior of the filter housing 110. The fluid delivery conduit 108, the filter 112, and the filter housing 110 can be configured such that the sample 104 comprising the infectious agent 102 is deposited or otherwise introduced on the filter surface 126 of the filter 112. The fluid delivery conduit 108 can also be configured such that enough fluid is delivered, injected, pumped, or otherwise introduced into the filter housing 110 such that the filter 112 (including the filter surface 126) is in fluid communication or in fluid communication with the sensor 114.

At least one parameter analyzer 120 coupled to the first sensor 122 can monitor an ORP of the first solution 140 in fluid communication with the first sensor 122. The ORP of the first solution 140 can be referred to as the first ORP. In addition, the same parameter analyzer 120 or another parameter analyzer coupled to the second sensor 124 can monitor an ORP of the second solution 142. The ORP of the second solution 142 can be referred to as the second ORP. The first ORP and the second ORP can be monitored in the absence of any added or exogenous reporter molecules in either the first solution 140 or the second solution 142 to assess the susceptibility of the infectious agent 102 to the anti-infective 106.

The first solution 140 and the second solution 142 can each have a solution characteristic. The solution characteristics of the first solution 140 and the second solution 142 can change as the amount of electro-active redox species changes due to the energy use, oxygen uptake or release, growth, or metabolism of the infectious agents 102 isolated or trapped by the filters 112. For example, the amount of electro-active redox species in the first solution 140 can change as a result of cellular activity undertaken by the infectious agents 102 captured by the first filter 130. Also, for example, the amount of electro-active redox species in the second solution 142 can change as a result of cellular activity undertaken by the infectious agents 102 captured by the second filter 134. As a more specific example, the amount of electron donors from Table 1 (e.g., the amount of energy carriers such as nicotinamide adenine dinucleotide (NADH) and flavin adenine dinucleotide ($FADH_2$)) in the first solution 140 or the second solution 142 can change due to the growth or lack thereof of the infectious agents 102 captured by the first filter 130 or the second filter 134. Also, as another more specific example, the amount of oxygen depleted in the first solution 140 or the second solution 142 due to aerobic respiration can change due to the growth or lack thereof of the infectious agents 102 captured by the first filter 130 or the second filter 134.

The parameter analyzer 120 or another device, such as the reader 116, coupled to the parameter analyzer 120 can be configured to compare the first ORP with the second ORP to assess the susceptibility of the infectious agent 102 in the sample 104 to the anti-infective 106 in step 2F. The parameter analyzer 120 or the reader 116 can compare the first ORP with the second ORP over a period of time. The period of time can be referred to as a detection window 160. The parameter analyzer 120 or the reader 116 can assess the susceptibility of the infectious agent 102 to the anti-infective 106 within the detection window 160. In one embodiment, the detection window 160 can be between 60 minutes and 120 minutes. In other embodiments, the detection window 160 can be between 5 minutes and 60 minutes. In additional embodiments, the detection window 160 can be greater than 120 minutes.

In one embodiment, the parameter analyzer 120 or the reader 116 can comprise a controller or processors to execute logical commands concerning the comparison of the first ORP with the second ORP and to generate a read-out or signal concerning a result of the comparison or detection.

For example, the parameter analyzer 120 or the reader 116 can determine or assess the susceptibility of the infectious agent 102 in the sample 104 as resistant to the anti-infective 106 when the parameter analyzer 120 or the reader 116 fails to detect certain statistically significant differences between the first ORP and the second ORP. This statistically significant difference can be a difference exceeding a threshold value. Conversely, the parameter analyzer 120 or the reader 116 can determine or assess the susceptibility of the infectious agent 102 as not resistant to the anti-infective 106 when the parameter analyzer 120 or the reader 116 detects certain statistically significant differences between the first ORP and the second ORP within the detection window 160.

In other embodiments, the parameter analyzer 120 or the reader 116 can assess the level of susceptibility of the infectious agent 102 in the sample 104 on a tiered scale. For example, the parameter analyzer 120 or the reader 116 can assess the susceptibility of the infectious agent 102 in the sample 104 as being resistant, of intermediate susceptibility, or susceptible to the anti-infective 106. In these embodiments, several first filter housings 128 can each comprise a different concentration of the anti-infective 106 to assess the level of susceptibility of the infectious agent 102 to the anti-infective 106.

The parameter analyzer 120 can also be connected to or communicatively coupled to a device having a display 162 or a display component configured to provide a result of the detection or a read-out of the electrical characteristic of the sensors 114. In certain embodiments, the reader 116 can be a mobile device, a handheld device, a tablet device, or a computing device such as a laptop or desktop computer and the display 162 can be a mobile device display, a handheld device display, a tablet display, or a laptop or desktop monitor. In some embodiments, the parameter analyzer 120 can wirelessly communicate a signal or result to the reader 116 or another computing device having the display 162.

The steps depicted in FIG. 2 do not require the particular order shown to achieve the desired result. Moreover, certain steps or processes may be omitted or occur in parallel in order to achieve the desired result.

Figure 3:
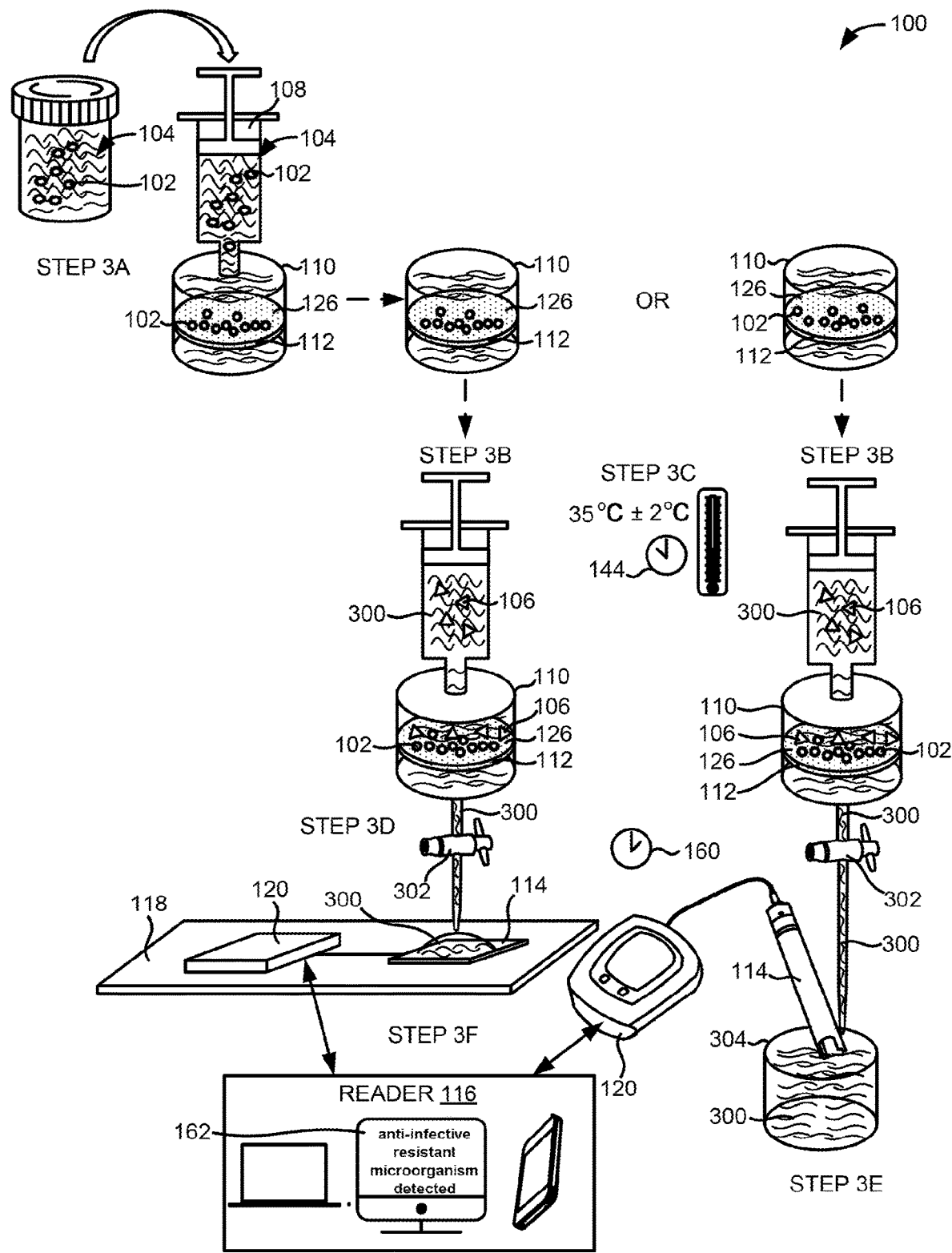
FIG. 3 illustrates yet another embodiment of a system for detecting a susceptibility of an infectious agent to one or more anti-infectives.

FIG. 3 illustrates another embodiment of the system 100 for detecting or assessing the susceptibility of an infectious agent 102 to an anti-infective 106. The system 100 can comprise a plurality of fluid delivery conduits 108, a filter housing 110 containing a filter 112, one or more sensors 114, and a reader 116. The system 100 shown in FIG. 3 can comprise the same fluid delivery conduits 108, sensors 114, filter housings 110, filters 112, readers 116, and parameter analyzers 120 as those shown in FIG. 1 or 2.

As illustrated in FIG. 3, the fluid delivery conduit 108 can deliver or inject the sample 104 into the filter housing 110 in step 3A. In another embodiment not shown in FIG. 3, a stimulus solution can be added to the sample 104 before introducing the sample 104 to the filter 112. The stimulus solution can be a nutrient or growth solution.

In an alternative embodiment not shown in FIG. 3, the sample 104 can be pre-filtered before step 3A. This pre-filtering step can involve filtering the sample 104 using another instance of a filter, a microfluidic filter, or a combination thereof to filter out debris, inorganic material, and larger cellular components including blood cells or epithelial cells from the sample 104.

Although FIG. 3 shows the fluid delivery conduit 108 delivering or injecting the sample 104 into one instance of the filter housing 110 containing the filter 112 in step 3A, it should be understood by one of ordinary skill in the art that the fluid delivery conduit 108 can deliver or inject the sample 104 into multiple instances of the filter housing 110 with each filter housing 110 containing its own filter 112.

The same fluid delivery conduit 108 or another fluid delivery conduit can then be used to deliver or inject a nutrient solution 300 to the filter housing 110 in step 3B. The nutrient solution 300 can comprise at least one anti-infective 106. In one embodiment, the nutrient solution 300 can be a solution containing bacto-tryptone, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose, or a combination thereof. In another embodiment, the nutrient solution 300 can include a growth inducer. The growth inducer can comprise a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the nutrient solution 300 can comprise Tryptone, yeast extract, sodium chloride, and glucose. The nutrient solution 300 can be used to counteract the buffering effects of ions or substances present in the sample 104 when the sample 104 is composed of a bodily fluid.

In some embodiments, a nutrient solution 300 without any anti-infectives 106 can initially be injected, pumped, or otherwise delivered to the filter housing 110 in step 3B. In these embodiments, anti-infectives 106 can be subsequently added to the flow of nutrient solution 300 or added to subsequent aliquots or injections of the nutrient solution 300 delivered to the filter housing 110.

The anti-infective 106 can comprise a bacteriostatic anti-infective, a bactericidal anti-infective, an anti-fungal anti-infective, or a combination thereof. In certain embodiments, the bacteriostatic anti-infective can comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, anti-fungals, or a combination or derivation thereof. The anti-fungals can comprise Amphotericin B, Flucytosine, Fluconazole, Ketoconazole, Itraconazole, Posaconazole, Ravuconazole, Voriconazole, or a combination thereof.

In some embodiments, a bacterial growth inhibitor or stimulator can also be added to the nutrient solution. The bacterial growth inhibitor or stimulator can selectively inhibit or promote the growth of gram positive or gram negative bacteria. The bacterial growth inhibitor can comprise a dye or a chemical compound or reagent. In some embodiments, the dye can include, but is not limited to, methylene blue, bromothymol blue, Eosin B, Safranin O, Crystal violet, colistin, nalidixic acid, yeast extract peptone dextrose (YEPD), bismuth ammonium citrate, sodium sulfite, or a combination thereof. The chemical compound or reagent can include, but is not limited to, sodium azide, bile salts, sodium chloride, tetrathionate, or a combination thereof.

The filter 112 can then be heated to a temperature of between 30° C. and 40° C. (e.g., 35° C.±2° C.) and allowed to incubate for an incubation period 144 in step 3C. The incubation period 144 can range from 15 minutes to over one hour. In other embodiments, the incubation period 144 can be less than 15 minutes or up to 48 hours.

The incubation period 144 can be adjusted based on the type of infectious agent 102 suspected in the sample 104, such as the type of bacteria or fungus. The incubation period 144 can also be adjusted based on the type of anti-infective 106, the mechanism of action of the anti-infective 106, the amount of the sample 104, or a combination thereof. The incubation period 144 can also be start-delayed or a pre-incubation time period can be added before the start of the incubation period 144. The start-delay or the pre-incubation time period can be added for slower acting drugs or anti-infectives 106 (e.g., β-lactams). In some embodiments, the start-delay or the pre-incubation time period can be between 10 minutes and 2 hours. In other embodiments, the start-delay or the pre-incubation time period can be as long as needed for the drug or anti-infective 106 to take effect. During the start-delay or pre-incubation time period, readings or measurements from the sensor 114 would not be used or would not be included as part of any growth curves generated. The start-delay or the pre-incubation time period is particularly useful for instances where higher inoculums or a higher concentration of infectious agents 102 is present in the sample 104 or isolated on the filter 112 and where the signal is generated quite fast in comparison to the mode of action of the drug or anti-infective 106.

In one embodiment, the filter 112 can be incubated while in the filter housing 110. In another embodiment, the filter 112 can be removed from the filter housing 110 prior to incubation. In some embodiments, the filter 112 can be incubated while in fluid communication with the nutrient solution 300 comprising the anti-infective 106. Benefits of incubating the filter 112 include speeding up the kinetics of the mechanism of action of the anti-infective 106, providing the infectious agent 102 time to grow, or a combination thereof.

After or while incubating the filter 112 in step 3C, at least a portion of the nutrient solution 300 previously in fluid communication with the filter surface 126 can be separated from the filter 112. For example, the filter housing 110 can comprise an opening, channel, or outlet for evacuating or siphoning the nutrient solution 300 previously in fluid communication with the filter surface 126 from the filter housing 110. The portion of the nutrient solution 300 separated from the filter surface 126 can then be directed or introduced to an instance of the sensor 114 fabricated or located on a substrate 118 in step 3D. As shown in FIG. 3, the sensor 114 can be a sensor on a test strip, an integrated circuit, or a micro-electro-mechanical system (MEMS) device. Moreover, in some embodiments, at least a part of the parameter analyzer 120 can also be integrated with the substrate 118.

The system 100 can also comprise a separation valve 302 configured to separate the portion of the nutrient solution 300 in fluid communication with the sensor 114 from the portion of the nutrient solution 300 still in fluid communication with the filter surface 126. In one embodiment, the separation valve 302 can comprise or be a two-way or three-way stopcock valve, a pinch valve, a push button valve, a needle valve, a microfluidic valve, or a combination thereof. In some variations, a stopper, a barrier, a cap, a plug of air, or a combination thereof can be used in lieu of or in addition to the separation valve 302. When a plug of air is used in lieu of the separation valve 302, certain components of the system 100 can be agitated.

A parameter analyzer 120 coupled to the sensor 114 can monitor an ORP of the nutrient solution 300 in fluid communication with the sensor 114. The ORP of the nutrient solution 300 can be monitored in the absence of any added or exogenous reporter molecules in the nutrient solution 300 to assess the susceptibility of the infectious agent 102 to the anti-infective 106.

While FIG. 3 illustrates only one sensor 114 on the substrate 118 being used to analyze solutions previously in contact with the infectious agents 102, it is contemplated by this disclosure that the substrate 118 can accommodate any number of sensors 114. For example, the substrate 118 can be a support or housing for a high throughput assay plate or well plate such as a 96 well plate, a 192 well plate, or a 384 well plate. In this example, each of the wells of the well plate can comprise or be in fluid communication with one or more sensors 114.

In an alternative embodiment shown in FIG. 3, after or while incubating the filter 112 in step 3C, at least a portion of the nutrient solution 300 previously in fluid communication with the filter surface 126 can be separated from the filter surface 126. For example, the filter housing 110 can comprise an opening, channel, or outlet for evacuating or siphoning the nutrient solution 300 previously in fluid communication with the filter surface 126 from the filter 112. The portion of the nutrient solution 300 separated from the filter surface 126 can then be directed or introduced to a measurement container 304 in step 3E.

The measurement container 304 can be a separate container or housing than the filter housing 110. The nutrient solution 300 can then be monitored by directly immersing at least part of a handheld or probe instance of the sensor 114 into the nutrient solution 300. For example, the handheld or probe instance of the sensor 114 can be an ORP sensor coupled to a standalone parameter analyzer 120 such as a voltmeter or multimeter.

The nutrient solution 300 can have a solution characteristic. The solution characteristics of the nutrient solution 300 can change as the amount of electro-active redox species changes due to the energy use, oxygen uptake or release, growth, or metabolism of the infectious agents 102 isolated or trapped by the filters 112. For example, the amount of electro-active redox species in the nutrient solution 300 can change as a result of cellular activity undertaken by the infectious agents 102 captured by the filters 112. As a more specific example, the amount of electron donors (e.g., the amount of energy carriers such as nicotinamide adenine dinucleotide (NADH) and flavin adenine dinucleotide ($FADH_2$)) in the nutrient solution 300 can change due to the growth or lack thereof of the infectious agents 102 captured by the filter 112. Also, as another more specific example, the amount of oxygen depleted in the nutrient solution 300 can change due to the growth or lack thereof of the infectious agents 102 captured by the filter 112.

The parameter analyzer 120 or another device, such as the reader 116, coupled to the parameter analyzer 120 can be configured to analyze a change in the ORP of the nutrient solution 300 to assess the susceptibility of the infectious agent 102 in the sample 104 to the anti-infective 106 in step 3F. For example, the parameter analyzer 120 or the reader 116 can monitor a change in the ORP of the nutrient solution 300 over a period of time. The period of time can be referred to as a detection window 160. The parameter analyzer 120 or the reader 116 can assess the susceptibility of the infectious agent 102 to the anti-infective 106 within the detection window 160. In one embodiment, the detection window 160 can be between 60 minutes and 120 minutes. In other embodiments, the detection window 160 can be between 5 minutes and 60 minutes. In additional embodiments, the detection window 160 can be greater than 120 minutes.

In one embodiment, the parameter analyzer 120 or the reader 116 can comprise a controller or processors to execute logical commands concerning the analysis of the solution ORP over time and to generate a read-out or signal concerning a result of the detection.

For example, the parameter analyzer 120 or the reader 116 can determine or assess the susceptibility of the infectious agent 102 in the sample 104 as resistant to the anti-infective 106 when the parameter analyzer 120 or the reader 116 fails to detect certain statistically significant changes in the ORP of the nutrient solution 300 over time. This statistically significant difference can be a difference exceeding a threshold value. Conversely, the parameter analyzer 120 or the reader 116 can determine or assess the susceptibility of the infectious agent 102 as not resistant to the anti-infective 106 when the parameter analyzer 120 or the reader 116 detects certain statistically significant changes in the ORP of the nutrient solution 300 within the detection window 160.

In other embodiments, the parameter analyzer 120 or the reader 116 can assess the level of susceptibility of the infectious agent 102 in the sample 104 on a tiered scale. For example, the parameter analyzer 120 or the reader 116 can assess the susceptibility of the infectious agent 102 in the sample 104 as being resistant, of intermediate susceptibility, or susceptible to the anti-infective 106. In these embodiments, several filter housings 110 can each comprise a different concentration of the anti-infective 106 to assess the level of susceptibility of the infectious agent 102 to the anti-infective 106.

The parameter analyzer 120 can also be connected to or communicatively coupled to a device having a display 162 or a display component configured to provide a result of the detection or a read-out of the electrical characteristic of the sensors 114. In certain embodiments, the reader 116 can be a mobile device, a handheld device, a tablet device, or a computing device such as a laptop or desktop computer and the display 162 can be a mobile device display, a handheld device display, a tablet display, or a laptop or desktop monitor. In some embodiments, the parameter analyzer 120 can wirelessly communicate a signal or result to the reader 116 or another computing device having the display 162.

The steps depicted in FIG. 3 do not require the particular order shown to achieve the desired result. Moreover, certain steps or processes may be omitted or occur in parallel in order to achieve the desired result.

Figure 4:
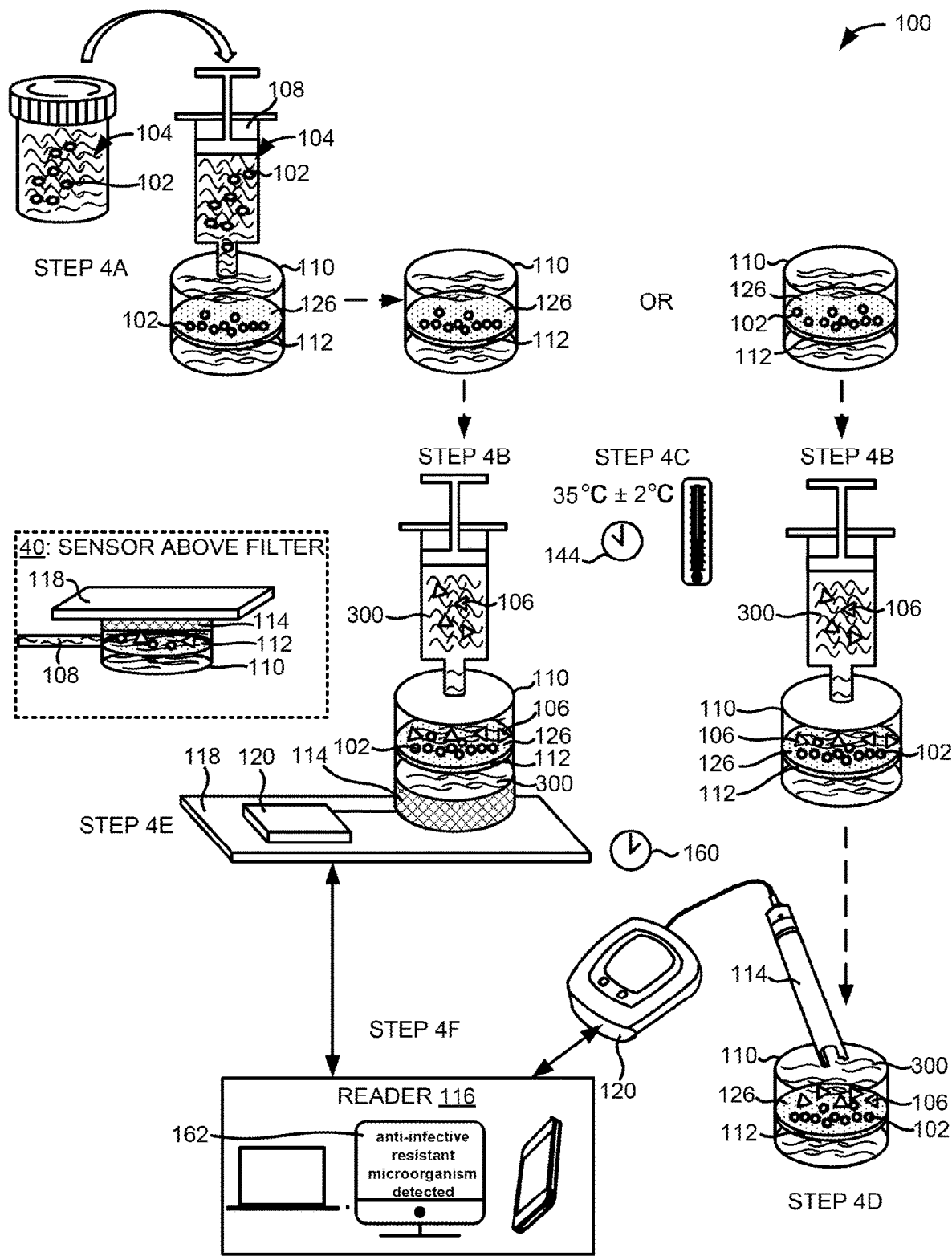
FIG. 4 illustrates a further embodiment of a system for detecting a susceptibility of an infectious agent to one or more anti-infectives.

FIG. 4 illustrates another embodiment of the system 100 for detecting or assessing the susceptibility of an infectious agent 102 to an anti-infective 106. The system 100 can comprise a plurality of fluid delivery conduits 108, a filter housing 110 containing a filter 112, one or more sensors 114, and a reader 116. The system 100 shown in FIG. 4 can comprise the same fluid delivery conduits 108, sensors 114, filter housings 110, filters 112, readers 116, and parameter analyzers 120 as those shown in FIGS. 1-3.

As illustrated in FIG. 4, the fluid delivery conduit 108 can deliver or inject the sample 104 into the filter housing 110 in step 4A. In another embodiment not shown in FIG. 4, a stimulus solution can be added to the sample 104 before introducing the sample 104 to the filter 112. The stimulus solution can be a nutrient or growth solution.

In an alternative embodiment not shown in FIG. 4, the sample 104 can be pre-filtered before step 4A. This pre-filtering step can involve filtering the sample 104 using another instance of a filter, a microfluidic filter, or a combination thereof to filter out debris, inorganic material, and larger cellular components including blood cells or epithelial cells from the sample 104.

Although FIG. 4 shows the fluid delivery conduit 108 delivering or injecting the sample 104 into one instance of the filter housing 110 containing the filter 112 in step 4A, it should be understood by one of ordinary skill in the art that the fluid delivery conduit 108 can deliver or inject the sample 104 into multiple instances of the filter housing 110 with each filter housing 110 containing its own filter 112.

The same fluid delivery conduit 108 or another fluid delivery conduit can then be used to deliver or inject a nutrient solution 300 to the filter housing 110 in step 4B. The nutrient solution 300 can comprise at least one anti-infective 106. In one embodiment, the nutrient solution 300 can be a solution containing bacto-tryptone, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose, or a combination thereof. In another embodiment, the nutrient solution 300 can include a growth inducer. The growth inducer can comprise a carbon-based inducer, a nitrogen-based inducer, a mineral, a trace element, a biological growth factor, or any combination thereof. For example, the growth stimulator or stimulus solution can include but is not limited to glucose, ammonia, magnesium, blood, or a combination thereof. In one example embodiment, the nutrient solution 300 can comprise Tryptone, yeast extract, sodium chloride, and glucose. The nutrient solution 300 can be used to counteract the buffering effects of ions or substances present in the sample 104 when the sample 104 is composed of a bodily fluid.

In some embodiments, a nutrient solution 300 without any anti-infectives 106 can initially be injected, pumped, or otherwise delivered to the filter housing 110 in step 4B. In these embodiments, anti-infectives 106 can be subsequently added to the flow of nutrient solution 300 or added to subsequent aliquots or injections of the nutrient solution 300 delivered to the filter housing 110.

The anti-infective 106 can comprise a bacteriostatic anti-infective, a bactericidal anti-infective, an anti-fungal anti-infective, or a combination thereof. In certain embodiments, the bacteriostatic anti-infective can comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, anti-fungals, or a combination or derivation thereof. The anti-fungals can comprise Amphotericin B, Flucytosine, Fluconazole, Ketoconazole, Itraconazole, Posaconazole, Ravuconazole, Voriconazole, or a combination thereof.

In some embodiments, a bacterial growth inhibitor or stimulator can also be added to the nutrient solution. The bacterial growth inhibitor or stimulator can selectively inhibit or promote the growth of gram positive or gram negative bacteria. The bacterial growth inhibitor can comprise a dye or a chemical compound or reagent. In some embodiments, the dye can include, but is not limited to, methylene blue, bromothymol blue, Eosin B, Safranin O, Crystal violet, colistin, nalidixic acid, yeast extract peptone dextrose (YEPD), bismuth ammonium citrate, sodium sulfite, or a combination thereof. The chemical compound or reagent can include, but is not limited to, sodium azide, bile salts, sodium chloride, tetrathionate, or a combination thereof.

The filter 112 can then be heated to a temperature of between 30° C. and 40° C. (e.g., 35° C.±2° C.) and allowed to incubate for an incubation period 144 in step 4C. The incubation period 144 can range from 15 minutes to over one hour. In other embodiments, the incubation period 144 can be less than 15 minutes.

The incubation period 144 can be adjusted based on the type of infectious agent 102 suspected in the sample 104, such as the type of bacteria or fungus. The incubation period 144 can also be adjusted based on the types of anti-infectives 106, the mechanism of action of the anti-infective 106, the amount of the sample 104, or a combination thereof. The incubation period 144 can also be start-delayed or a pre-incubation time period can be added before the start of the incubation period 144. The start-delay or the pre-incubation time period can be added for slower-acting drugs or anti-infectives 106 (e.g., β-lactams). In some embodiments, the start-delay or the pre-incubation time period can be between 10 minutes and 2 hours. In other embodiments, the start-delay or the pre-incubation time period can be as long as needed for the drug or anti-infective 106 to take effect. During the start-delay or pre-incubation time period, readings or measurements from the sensor 114 would not be used or would not be included as part of any growth curves generated. The start-delay or the pre-incubation time period is particularly useful for instances where higher inoculums or a higher concentration of infectious agents 102 is present in the sample 104 or isolated on the filter 112 and where the signal is generated quite fast in comparison to the mode of action of the drug or anti-infective 106.

In one embodiment, the filter 112 can be incubated while in the filter housing 110. In another embodiment, the filter 112 can be removed from the filter housing 110 prior to incubation. In some embodiments, the filter 112 can be incubated while in fluid communication with the nutrient solution 300 comprising the anti-infective 106. Benefits of incubating the filter 112 include speeding up the kinetics of the mechanism of action of the anti-infective 106, providing the infectious agent 102 time to grow, or a combination thereof.

After or while incubating the filter 112 in step 4C, the nutrient solution 300 within the filter housing 110 in fluid communication with the filter surface 126 can be monitored by directly immersing at least part of a handheld or probe instance of the sensor 114 into the nutrient solution 300 in step 4D. For example, the handheld or probe instance of the sensor 114 can be an ORP sensor coupled to a standalone parameter analyzer 120 such as a voltmeter or multimeter.

Alternatively, as shown in FIG. 4, the filter housing 110 can be directly coupled to or fabricated on a substrate 118 comprising at least one sensor 114. For example, at least one sensor 114 can be a sensor on a test strip, an integrated circuit, or a micro-electro-mechanical system (MEMS) device. Moreover, in some embodiments, at least a part of the parameter analyzer 120 can also be integrated with the substrate 118. In this embodiment, the nutrient solution 300 can be monitored by the sensor 114 coupled to or fabricated on the substrate 118 as soon as the nutrient solution 300 is delivered, injected, or otherwise introduced to the filter housing 110 in step 4E.

While FIG. 4 illustrates only one sensor 114 on the substrate 118 being used to analyze solutions previously in contact with the infectious agents 102, it is contemplated by this disclosure that the substrate 118 can accommodate any number of sensors 114. For example, the substrate 118 can be a support or housing for a high throughput assay plate or well plate such as a 96 well plate, a 192 well plate, or a 384 well plate. In this example, each of the wells of the well plate can comprise or be in fluid communication with one or more sensors 114.

Moreover, inset 40 illustrates an alternative embodiment where the sensor 114 is positioned vertically above the filter housing 110 comprising the filter 112. In this embodiment, the fluid delivery conduit 108 can deliver, inject, pump, or otherwise introduce the sample 104, a solution carrying the sample 104, or any other solutions into the interior of the filter housing 110. The fluid delivery conduit 108, the filter 112, and the filter housing 110 can be configured such that the sample 104 comprising the infectious agent 102 is deposited or otherwise introduced on the filter surface 126 of the filter 112. The fluid delivery conduit 108 can also be configured such that enough fluid is delivered, injected, pumped, or otherwise introduced into the filter housing 110 such that the filter 112 (including the filter surface 126) is in fluid communication or in fluid communication with the sensor 114.

At least one parameter analyzer 120 coupled to the sensor 114 can monitor an ORP of the nutrient solution 300 in fluid communication with the sensor 114. The ORP of the nutrient solution 300 can be monitored in the absence of any added or exogenous reporter molecules in the nutrient solution 300 to assess the susceptibility of the infectious agent 102 to the anti-infective 106.

The nutrient solution 300 can have a solution characteristic. The solution characteristics of the nutrient solution 300 can change as the amount of electro-active redox species changes due to the energy use, oxygen uptake or release, growth, or metabolism of the infectious agents 102 isolated or trapped by the filters 112. For example, the amount of electro-active redox species in the nutrient solution 300 can change as a result of cellular activity undertaken by the infectious agents 102 captured by the filters 112. As a more specific example, the amount of electron donors (e.g., the amount of energy carriers such as nicotinamide adenine dinucleotide (NADH) and flavin adenine dinucleotide (FADH$_2$)) in the nutrient solution 300 can change due to the growth or lack thereof of the infectious agents 102 captured by the filter 112. Also, as another more specific example, the amount of oxygen depleted in the nutrient solution 300 can change due to the growth or lack thereof of the infectious agents 102 captured by the filter 112.

The parameter analyzer 120 or another device, such as the reader 116, coupled to the parameter analyzer 120 can be configured to analyze a change in the ORP of the nutrient solution 300 to assess the susceptibility of the infectious agent 102 in the sample 104 to the anti-infective 106 in step 4F. For example, the parameter analyzer 120 or the reader 116 can monitor a change in the ORP of the nutrient solution 300 over a period of time. The period of time can be referred to as a detection window 160. The parameter analyzer 120 or the reader 116 can assess the susceptibility of the infectious agent 102 to the anti-infective 106 within the detection window 160. In one embodiment, the detection window 160 can be between 60 minutes and 120 minutes. In other embodiments, the detection window 160 can be between 5 minutes and 60 minutes. In additional embodiments, the detection window 160 can be greater than 120 minutes.

In one embodiment, the parameter analyzer 120 or the reader 116 can comprise a controller or processors to execute logical commands concerning the analysis of the solution ORP over time and to generate a read-out or signal concerning a result of the detection.

For example, the parameter analyzer 120 or the reader 116 can determine or assess the susceptibility of the infectious agent 102 in the sample 104 as resistant to the anti-infective 106 when the parameter analyzer 120 or the reader 116 fails to detect certain statistically significant changes in the ORP of the nutrient solution 300 over time. This statistically significant difference can be a difference exceeding a threshold value. Conversely, the parameter analyzer 120 or the reader 116 can determine or assess the susceptibility of the infectious agent 102 as not resistant to the anti-infective 106 when the parameter analyzer 120 or the reader 116 detects certain statistically significant changes in the ORP of the nutrient solution 300 within the detection window 160.

In other embodiments, the parameter analyzer 120 or the reader 116 can assess the level of susceptibility of the infectious agent 102 in the sample 104 on a tiered scale. For example, the parameter analyzer 120 or the reader 116 can assess the susceptibility of the infectious agent 102 in the sample 104 as being resistant, of intermediate susceptibility, or susceptible to the anti-infective 106. In these embodiments, several filter housings 110 can each comprise a different concentration of the anti-infective 106 to assess the level of susceptibility of the infectious agent 102 to the anti-infective 106.

The parameter analyzer 120 can also be connected to or communicatively coupled to a device having a display 162 or a display component configured to provide a result of the detection or a read-out of the electrical characteristic of the sensors 114. In certain embodiments, the reader 116 can be a mobile device, a handheld device, a tablet device, or a computing device such as a laptop or desktop computer and the display 162 can be a mobile device display, a handheld device display, a tablet display, or a laptop or desktop monitor. In some embodiments, the parameter analyzer 120 can wirelessly communicate a signal or result to the reader 116 or another computing device having the display 162.

The steps depicted in FIG. 4 do not require the particular order shown to achieve the desired result. Moreover, certain steps or processes may be omitted or occur in parallel in order to achieve the desired result.

Figure 5A:
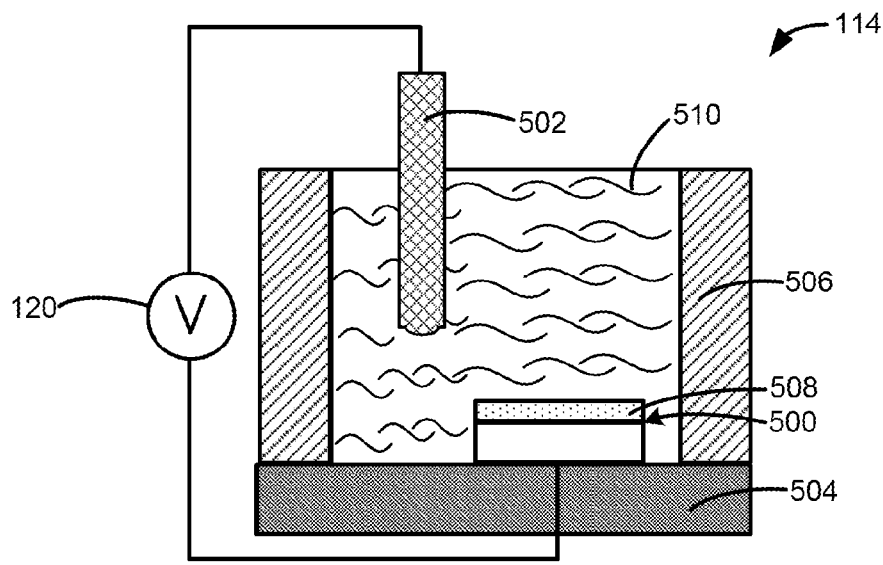
FIG. 5A illustrates a side view of an embodiment of a sensor having an active electrode and an on-chip reference electrode.

FIG. 5A illustrates a side view of one embodiment of the sensor 114. The sensor 114 can be any of the first sensor 122 or the second sensor 124. The sensor 114 can be an electrochemical cell comprising an active electrode 500 and an external reference electrode 502. In some embodiments of the sensor 114, the active electrode 500 and the external reference electrode 502 are the only electrodes of the sensor 114.

The active electrode 500 can extend from or be disposed on a substrate layer 504. The substrate layer 504 can be composed of, but is not limited to, any non-conducting material such as a polymer, an oxide, a ceramic, or a composite thereof. The electrochemical cell can be surrounded or contained by walls 506 configured to retain a sampled solution 510. The walls 506 can be made of an inert or non-conductive material.

The sampled solution 510 can refer to any of the first solution 140, the second solution 142, the nutrient solution 300, or a portion or aliquot thereof. The sampled solution 510 can be introduced to the sensor 114 from the filter housing 110, the first measurement container 150, the second measurement container 152, the measurement container 304, or any other container.

The external reference electrode 502 can be in fluid communication or communication with the sampled solution 510. For example, the external reference electrode 502 can extend into or be immersed in the sampled solution 510. The external reference electrode 502 can also have a stable or well-known internal voltage and the sensor 114 can use the external reference electrode 502 to determine or measure a relative change in the potential of the active electrode 500. In one embodiment, the external reference electrode 502 can be a standalone probe or electrode. In other embodiments, the external reference electrode 502 can be coupled to the parameter analyzer 120. In some embodiments, the first sensor 122 and the second sensor 124 can share and use the same external reference electrode 502.

In one embodiment, the external reference electrode 502 can be a silver/silver chloride (Ag/AgCl) electrode. In other embodiments, the external reference electrode 502 can comprise a saturated calomel reference electrode (SCE) or a copper-copper (II) sulfate electrode (CSE). The external reference electrode 502 can also be a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

The active electrode 500 can comprise multiple conductive layers (e.g., a stack of metallic layers) and a redox-active material 508 or layer such as a gold layer, a platinum layer, a metal oxide layer, a carbon layer, or a combination thereof on top of the multiple conductive layers. In some embodiments, the metal oxide layer can comprise an iridium oxide layer, a ruthenium oxide layer, or a combination thereof. The parameter analyzer 120 can be coupled to the active electrode 500 and the external reference electrode 502.

The parameter analyzer 120 can determine the ORP of the sampled solution 510 by measuring the potential difference between the external reference electrode 502 and the active electrode 500 instantly or over a period of time (e.g., the detection window 160). As shown in FIG. 5A, the parameter analyzer 120 can be a voltmeter or any other type of high-impedance amplifier or sourcemeter. The voltmeter can measure a relative change in an equilibrium potential at an interface between the redox-active material 508 of the active electrode 500 and the sampled solution 510 containing electro-active redox species. The solution characteristic of the sampled solution 510 (e.g., the first solution 140, the second solution 142, the nutrient solution 300, etc.) can change as the amount of electro-active redox species changes due to the energy use, oxygen uptake or release, growth, or metabolism of the infectious agents 102 isolated or trapped by the filter 112. For example, the amount of electro-active redox species in the sampled solution 510 can change as a result of cellular activity undertaken by the infectious agents 102 captured by the filter 112. As a more specific example, the amount of electron donors from Table 1 (e.g., the amount of energy carriers such as nicotinamide adenine dinucleotide (NADH) and flavin adenine dinucleotide (FADH$_2$)) in the sampled solution 510 can change due to the growth or lack thereof of the infectious agents 102 captured by the filter 112. Also, as another more specific example, the amount of oxygen depleted in the sampled solution 510 can change due to the growth or lack thereof of the infectious agents 102 captured by the filter 112.

In one embodiment, the active electrode 500 can comprise a metallic layer. The metallic layer can comprise a gold layer, a platinum layer, or a combination thereof. The active electrode 500 can also comprise multiple layers comprising a semiconductor layer having a redox-active metal oxide layer, such as iridium oxide or ruthenium oxide on top of the multiple layers. In other embodiments, the active electrode 500 can comprise one or more metallic layers, one or more redox-active metal oxide layers, one or more semiconductor layers, or any combination or stacking arrangement thereof.

Figure 5B:
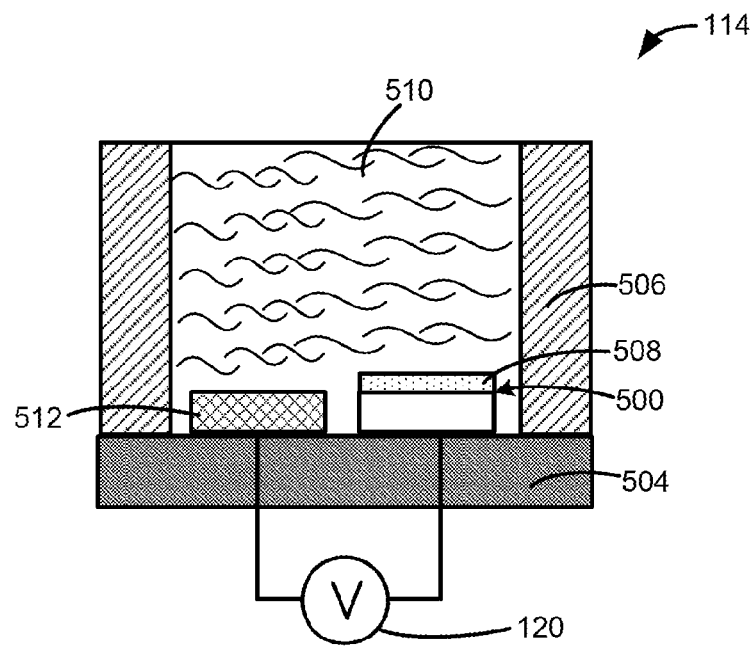
FIG. 5B illustrates a side view of another embodiment of a sensor having an active electrode and an external reference electrode.

FIG. 5B illustrates a side view of another embodiment of the sensor 114 having an on-chip reference electrode 512 disposed on the substrate layer 504 in lieu of the external reference electrode 502. In some embodiments of the sensor 114, the active electrode 500 and the on-chip reference electrode 512 are the only electrodes of the sensor 114.

In these and other embodiments, the on-chip reference electrode 512 can be coated by a polymeric coating. For example, the on-chip reference electrode 512 can be coated by a polyvinyl chloride (PVC) coating, a perfluorosulfonate coating (e.g., Nafion™), or a combination thereof.

The on-chip reference electrode 512 can serve the same purpose as the external reference electrode 502 except be fabricated on or integrated with the substrate layer 504. The on-chip reference electrode 512 can be located adjacent to or near the active sensor 120. The sensor 114 of FIG. 5B can serve the same function as the sensor 114 of FIG. 5A. Similar to the active electrode 500 of FIG. 5B, the on-chip reference electrode 512 can also be in fluid communication or communication with the sampled solution 510 retained within walls 506.

The on-chip reference electrode 512 can be comprised of a metal, a semiconductor material, or a combination thereof. The metal of the on-chip reference electrode 512 can be covered by an oxide layer, a silane layer, a polymer layer, or a combination thereof. In another embodiment, the on-chip reference electrode 512 can be a metal combined with a metal salt such as an Ag/AgCl on-chip reference electrode. In another embodiment, the on-chip reference electrode can be a miniaturized electrode with a well-defined potential. In some embodiments, the first sensor 122 and the second sensor 124 can share and use the same on-chip reference electrode 512. The on-chip reference electrode 512 can comprise a saturated calomel reference electrode (SCE) or a copper-copper (II) sulfate electrode (CSE). The on-chip reference electrode 512 can also comprise a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

Figure 6A:
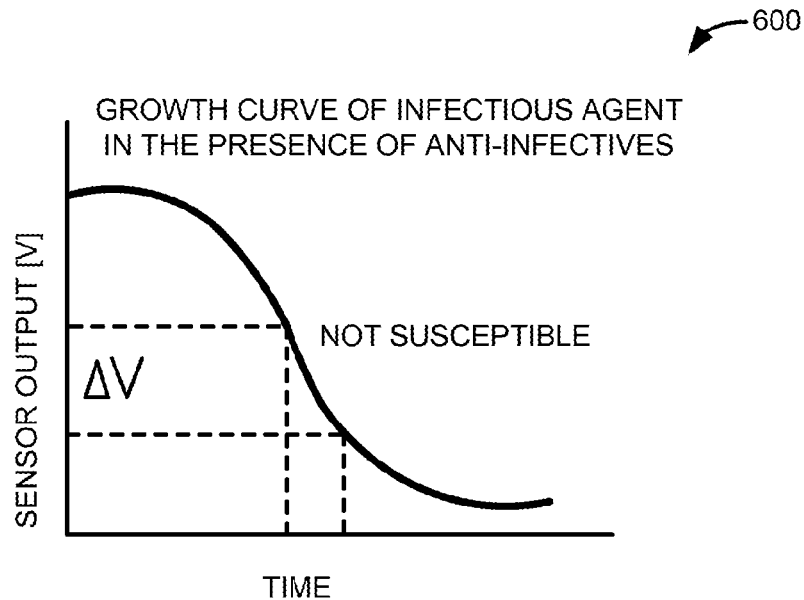
FIG. 6A illustrates a growth curve of an infectious agent resistant to one or more anti-infectives.

FIG. 6A illustrates an example growth curve 600 of an infectious agent 102 not susceptible or resistant to an anti-infective 106 in solution. The growth curve 602 can be recorded by monitoring the sensor output of the sensor 114 (including, but not limited to, the first sensor 122 or the second sensor 124) in fluid communication with the sampled solution 510 (i.e., the ORP of the sampled solution 510). In one embodiment, the sensor output can be a potential difference between the active electrode 500 and a reference electrode (e.g., the external reference electrode 502, the on-chip reference electrode 512, etc.). The sensor output of the sensor 114 can change as the ORP of the sampled solution 510 (e.g., any of the first solution 140, the second solution 142, the nutrient solution 300, etc.) changes.

The voltage output of the sensor 114 can change over time. For example, as shown in FIG. 6A, the voltage output of the sensor 114 can decrease over time as the solution characteristic of the sampled solution 510 changes due to the energy use, oxygen uptake or release, growth, or metabolism of the infectious agents 102 isolated or trapped by the filter(s) 112. In some embodiments, the change (e.g., decrease) in the voltage output of the sensor 114 can follow, but is not limited to, a sigmoidal pattern or shape or a step function or shape. Over longer time scales, the sensor output or voltage can begin to increase or become more positive.

For example, the voltage output of the sensor 114 can decrease over time as the solution characteristic of the sampled solution 510 changes as a result of cellular activity undertaken by the infectious agents 102 captured by the filter 112. As a more specific example, the solution characteristic of the sampled solution 510 can change as the amount of energy carriers (such as nicotinamide adenine dinucleotide (NADH) and flavin adenine dinucleotide (FADH$_2$)) in the sampled solution 510 changes due to the growth of the anti-infective resistant infectious agents 102. Also, as another more specific example, the amount of oxygen depleted in the sampled solution 510 can change due to the growth or lack thereof of the infectious agents 102 captured by the filter 112.

Figure 6B:
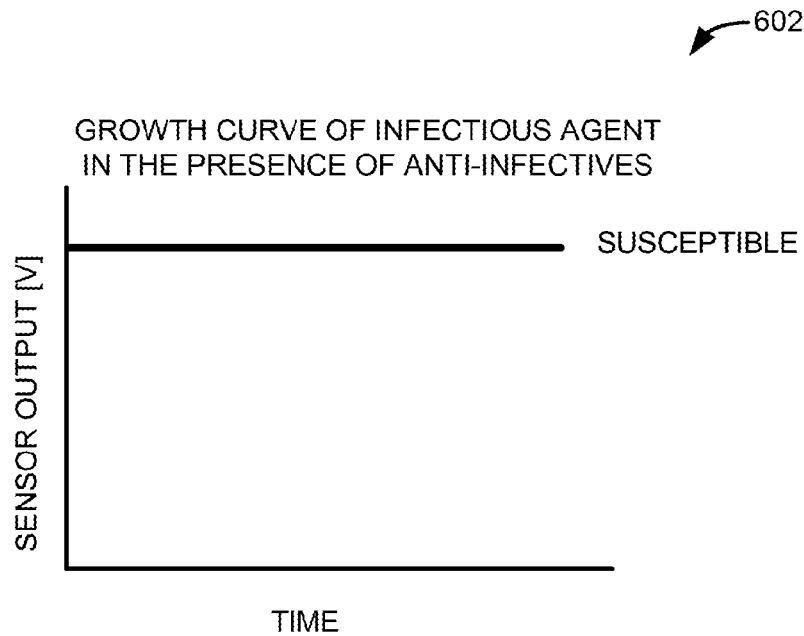
FIG. 6B illustrates a growth curve of an infectious agent susceptible to one or more anti-infectives.

FIG. 6B illustrates an example growth curve 602 of an infectious agent 102 susceptible to or not resistant to an anti-infective 106 in solution. The growth curve 602 can be recorded by monitoring the sensor output of the sensor 114 in fluid communication with the sampled solution 510 (i.e., the ORP of the sampled solution 510). As shown in FIG. 6B, the growth curve 602 can be relatively constant (e.g., a substantially flat line) or change very little. In other embodiments not shown in FIG. 6B, the growth curve 602 can exhibit changes within a predetermined threshold range. The sensor output of the sensor 114 can stay relatively constant as the ORP of the sampled solution 510 (e.g., any of the first solution 140, the second solution 142, the nutrient solution 300, etc.) stays relatively constant.

In one embodiment, the voltage output of the sensor 114 can be a potential difference between the active electrode 500 and a reference electrode such as the external reference electrode 502, the on-chip reference electrode 512, or another reference electrode.

The voltage output of the sensor 114 can stay relatively constant as the solution characteristic of the sampled solution 510 stays relatively constant due to the inhibitive effects of the anti-infective 106 on the infectious agents 102 isolated or trapped by the filter(s) 112.

Figure 6C:
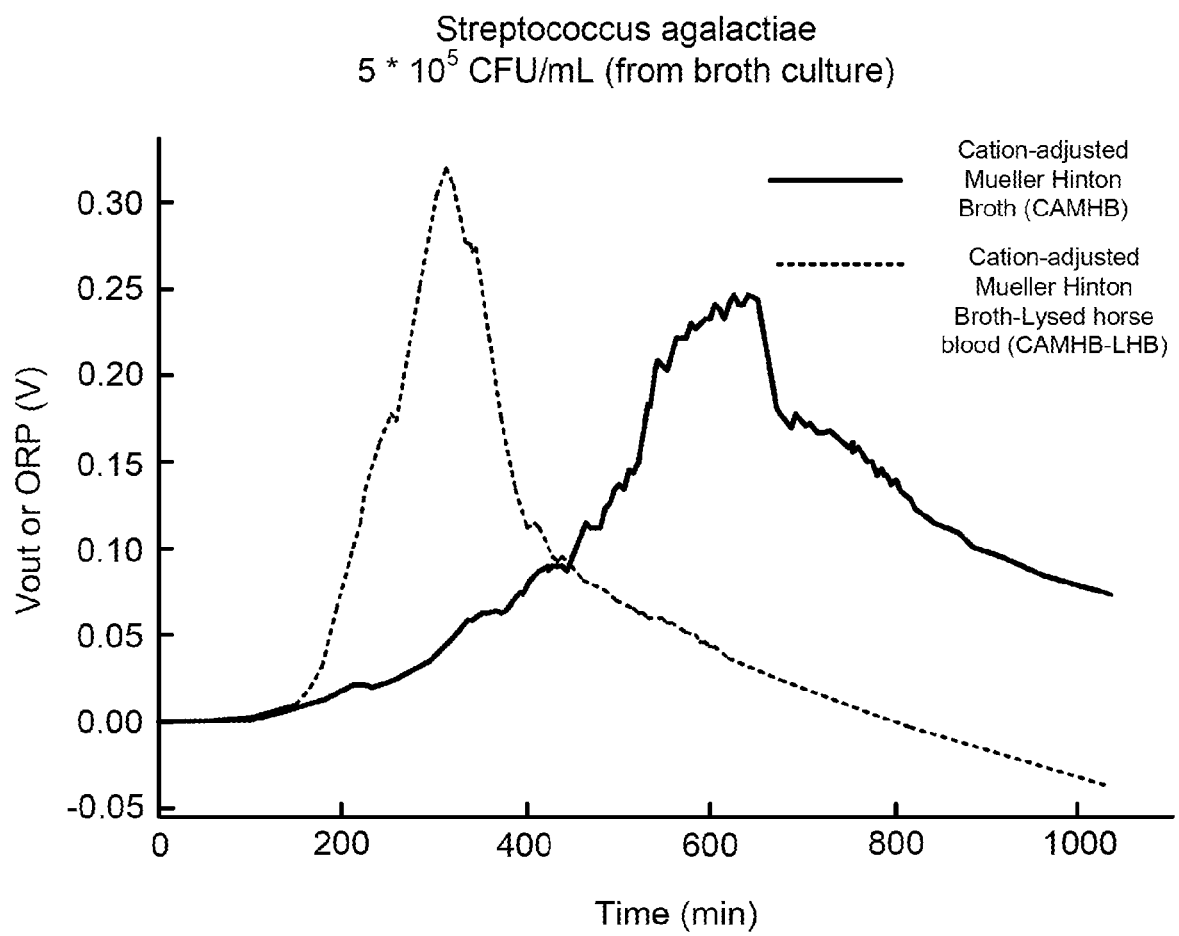
FIG. 6C illustrates a growth curve of an infectious agent.

FIG. 6C illustrates an example growth curve 604 of *Streptococcus agalactiae* bacteria in different media (e.g., CAMHB and CAMHB-LHB). The growth curve 604 can be recorded by monitoring the sensor output of the sensor 114 (including, but not limited to, the first sensor 122 or the second sensor 124) in fluid communication with the sampled solution 510 (i.e., the ORP of the sampled solution 510). In one embodiment, the sensor output can be a potential difference between the active electrode 500 and a reference electrode (e.g., the external reference electrode 502, the on-chip reference electrode 512, etc.). The sensor output of the sensor 114 can change as the ORP of the sampled solution 510 (e.g., any of the first solution 140, the second solution 142, the nutrient solution 300, etc.) changes.

The voltage output of the sensor 114 can change over time. For example, as shown in FIG. 6C, the voltage output of the sensor 114 can increase initially (e.g., when the software normalizes) and decrease over time before leveling out or staying relatively constant. Over longer time scales, the sensor output or voltage can begin to increase or become more positive.

Figure 7A:
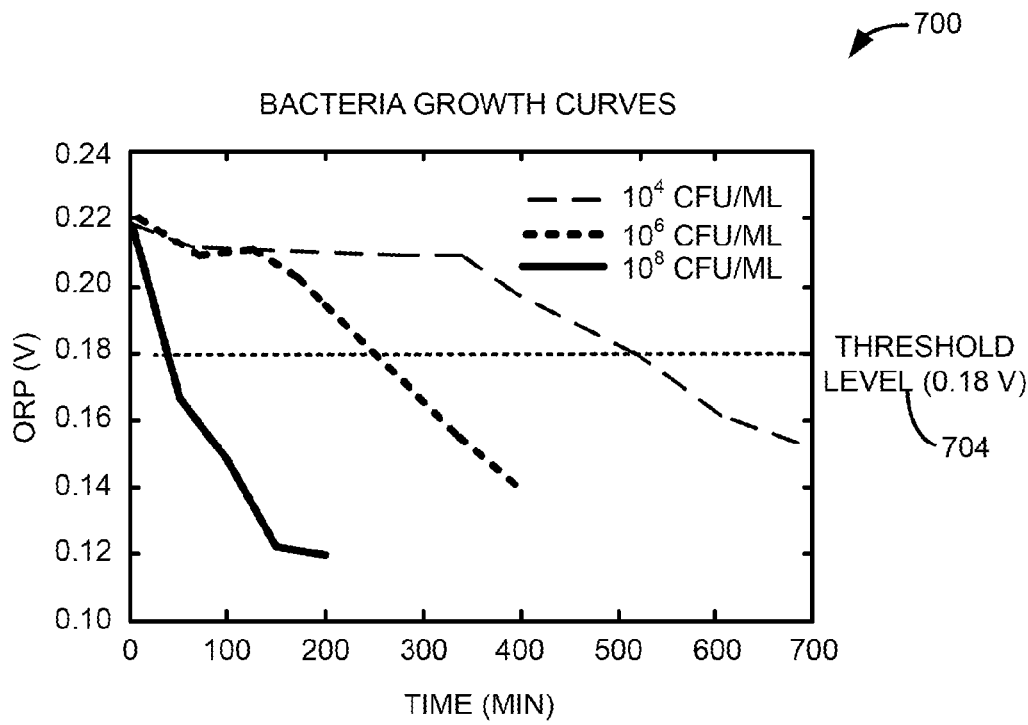
FIG. 7A illustrates experimental results of experiments conducted using the methods and systems described herein.

FIG. 7A illustrates results of experiments conducted using the methods and systems 100 described herein. The graph 700 of FIG. 7A shows the growth curves of different concentrations of *Pseudomonas aeruginosa* bacteria (expressed as colony-forming units/milliliter (CFU/mL)) by monitoring the change in the ORP of nutrient solutions exposed to the bacteria. For example, prepared samples 104 containing different concentrations of *Pseudomonas aeruginosa* bacteria were injected or otherwise introduced to the filters 112 described herein. The filters 112 were then washed or otherwise exposed to nutrient solutions. The bacteria growth curves were then recorded by monitoring the change in ORP of the nutrient solutions in fluid communication with the filters 112 over time. The ORP of the nutrient solutions were monitored using the sensors described herein including one or more ORP sensors.

Figure 7B:
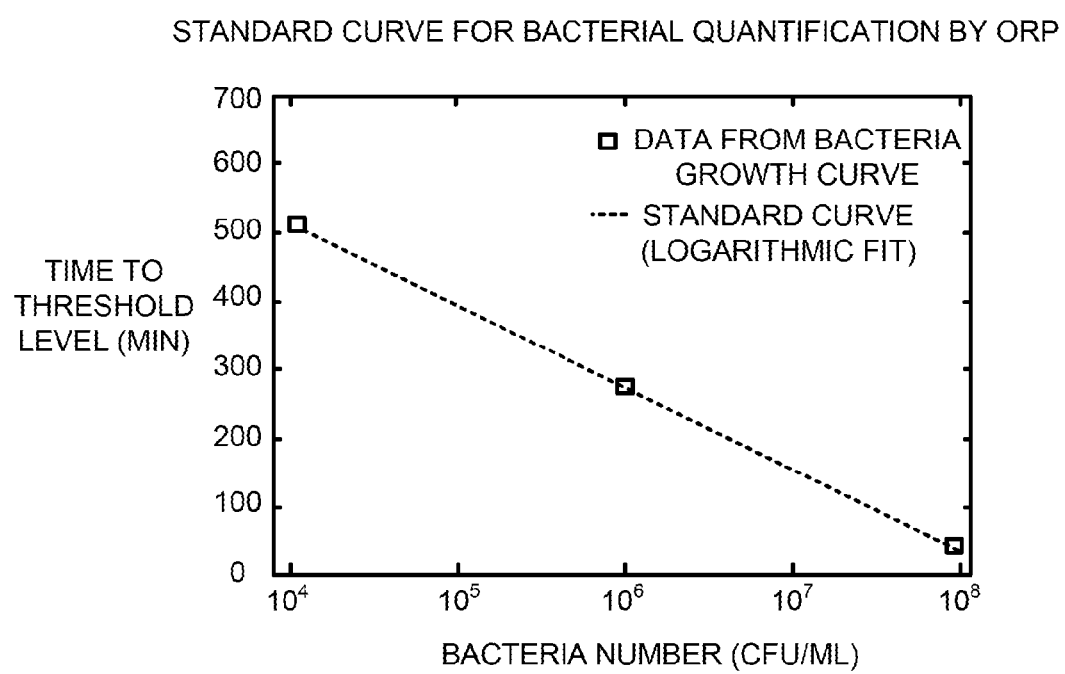
FIG. 7B illustrates a standard curve generated using experimental data obtained using the methods and systems described herein.

FIG. 7B illustrates a standard curve 702 generated using certain experimental data from the experiments described above. As shown in FIG. 7A, a threshold ORP level 704 was set at 0.18V. The time it took for the ORP of a sampled solution 510 to reach this threshold ORP level 704 was plotted as a function of the logarithm of the known concentration of the infectious agent 102 present in the prepared samples 104. A standard curve 702 can then be generated using curve fitting techniques such as logarithmic regression and least-squares. In other embodiments, polynomial and logarithmic curve fitting techniques can also be used.

As shown in FIG. 7B, a logarithmic standard curve 702 can be generated using the experimental data shown in FIG. 7A. Deriving an equation for this logarithmic standard curve 702 can then allow us to interpolate unknown concentrations of infectious agents 102 in sample 104 using only the time it took such a solution to reach the threshold ORP level 704.

Figure 8:
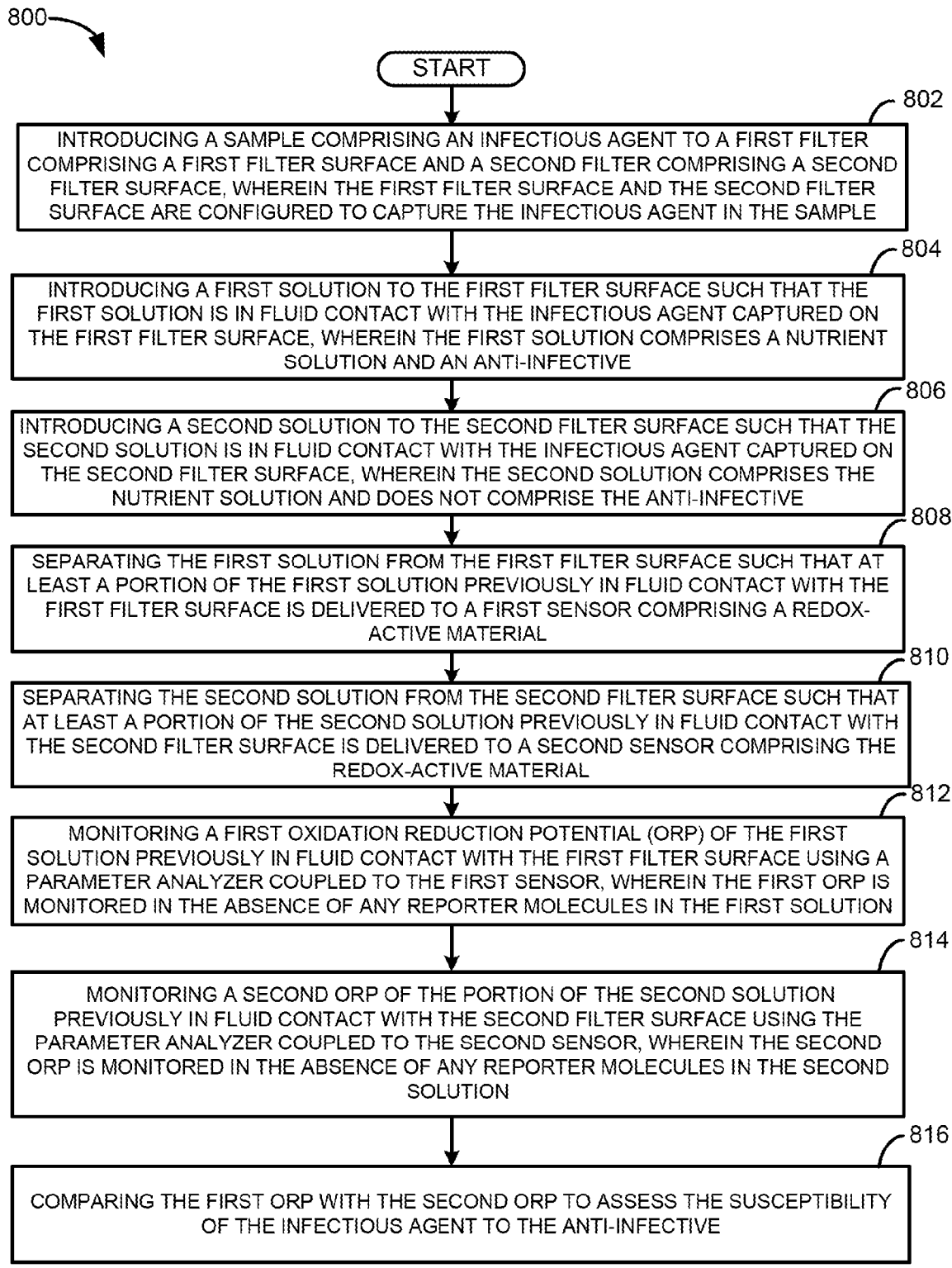
FIG. 8 illustrates an embodiment of a method for detecting a susceptibility of an infectious agent to one or more anti-infectives.

FIG. 8 illustrates an embodiment of a method 800 for detecting a susceptibility of an infectious agent 102 to one or more anti-infectives 106. The method 800 can involve introducing a sample 104 comprising an infectious agent 102 to a first filter 130 comprising a first filter surface 136 and a second filter 134 comprising a second filter surface 138, wherein the first filter surface 136 and the second filter surface 138 are configured to capture the infectious agent 102 in the sample in step 802.

The method 800 can also involve introducing a first solution 140 to the first filter surface 136 such that the first solution 140 is in fluid communication with the infectious agent 102 captured on the first filter surface 136, wherein the first solution 140 comprises a nutrient solution and an anti-infective 106 in step 804. The method 800 can also involve introducing a second solution 142 to the second filter surface 138 such that the second solution 142 is in fluid communication with the infectious agent 102 captured on the second filter surface 138, wherein the second solution 142 comprises the nutrient solution and does not comprise the anti-infective 106 in step 806.

The method 800 can further involve separating the first solution 140 from the first filter surface 136 such that at least a portion of the first solution 140 previously in fluid communication with the first filter surface 136 is delivered to a first sensor 122 comprising a redox-active material 508 in step 808. The method 800 can further involve separating the second solution 142 from the second filter surface 138 such that at least a portion of the second solution 142 previously in fluid communication with the second filter surface 138 is delivered to a second sensor 124 comprising the redox-active material 508 in step 810.

The method 800 can also involve monitoring a first ORP of the first solution 140 previously in fluid communication with the first filter surface 136 using at least one parameter analyzer 120 coupled to the first sensor 122, wherein the first ORP is monitored in the absence of any added or exogenous reporter molecules in the first solution 140 in step 812. The method 800 can also involve monitoring a second ORP of the portion of the second solution 142 previously in fluid communication with the second filter surface 138 using the parameter analyzer 120 coupled to the second sensor 124, wherein the second ORP is monitored in the absence of any added or exogenous reporter molecules in the second solution 142 in step 814. The method 800 can further involve comparing the first ORP with the second ORP to assess the susceptibility of the infectious agent 102 to the anti-infective 106 in step 816.

Figure 9:
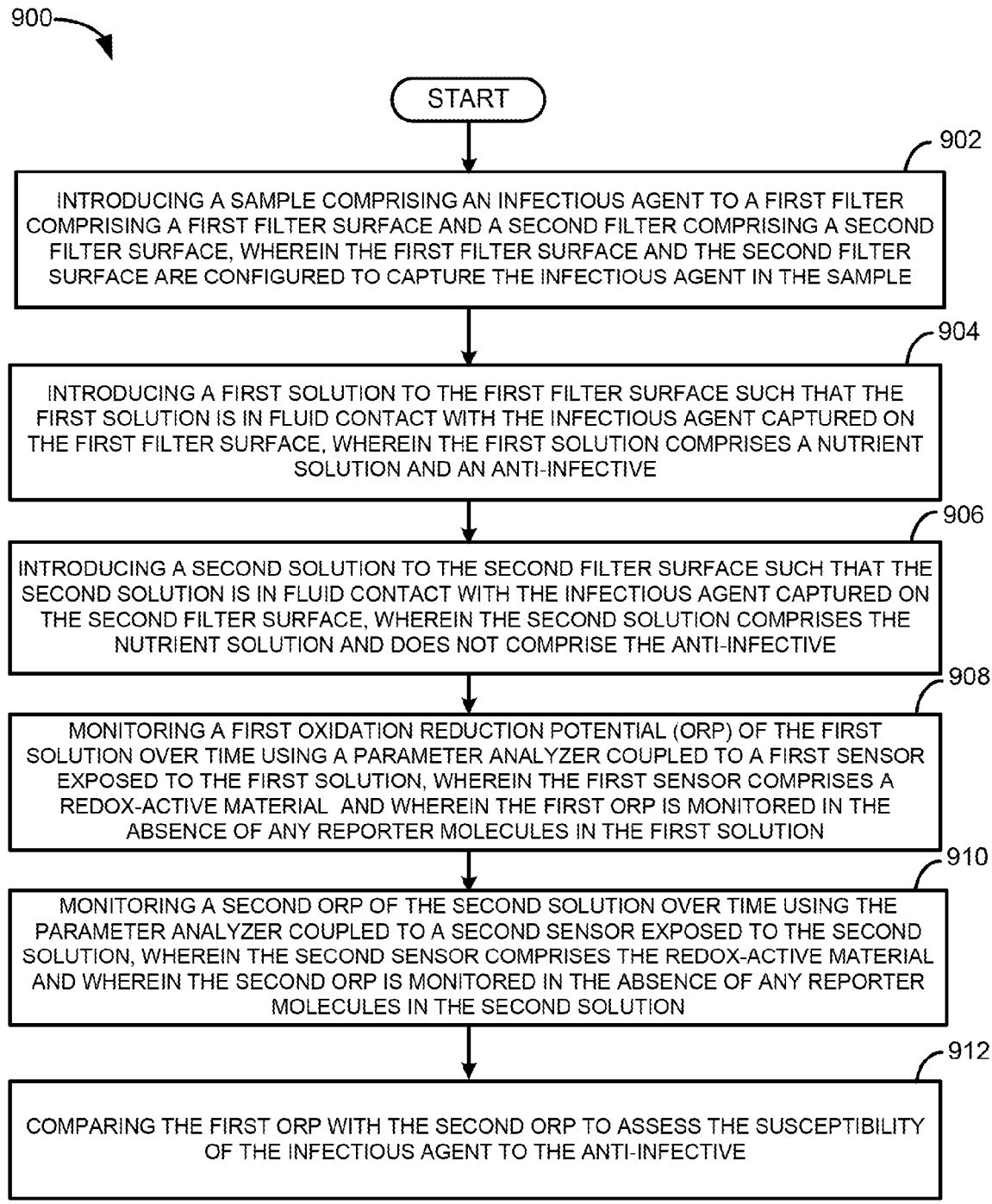
FIG. 9 illustrates another embodiment of a method for detecting a susceptibility of an infectious agent to one or more anti-infectives.

FIG. 9 illustrates another embodiment of a method 900 for detecting a susceptibility of an infectious agent 102 to one or more anti-infectives 106. The method 900 can involve introducing a sample 104 comprising an infectious agent 102 to a first filter 130 comprising a first filter surface 136 and a second filter 134 comprising a second filter surface 138, wherein the first filter surface 136 and the second filter surface 138 are configured to capture the infectious agent 102 in the sample in step 902.

The method 900 can also involve introducing a first solution 140 to the first filter surface 136 such that the first solution 140 is in fluid communication with the infectious agent 102 captured on the first filter surface 136, wherein the first solution 140 comprises a nutrient solution and an anti-infective 106 in step 904. The method 900 can also involve introducing a second solution 142 to the second filter surface 138 such that the second solution 142 is in fluid communication with the infectious agent 102 captured on the second filter surface 138, wherein the second solution 142 comprises the nutrient solution and does not comprise the anti-infective 106 in step 906.

The method 900 can further involve monitoring a first ORP of the first solution 140 over time using at least one parameter analyzer 120 coupled to a first sensor 122 exposed to the first solution 140, wherein the first sensor 122 comprises a redox-active material 508 and wherein the first ORP is monitored in the absence of any added or exogenous reporter molecules in the first solution 140 in step 908. The method 900 can further involve monitoring a second ORP of the second solution 142 over time using the parameter analyzer 120 coupled to a second sensor 124 exposed to the second solution 142, wherein the second sensor 124 comprises the redox-active material 508 and wherein the second ORP is monitored in the absence of any added or exogenous reporter molecules in the second solution 142 in step 910. The method 900 can also involve comparing the first ORP with the second ORP to assess the susceptibility of the infectious agent 102 to the anti-infective 106 in step 912.

Figure 10:
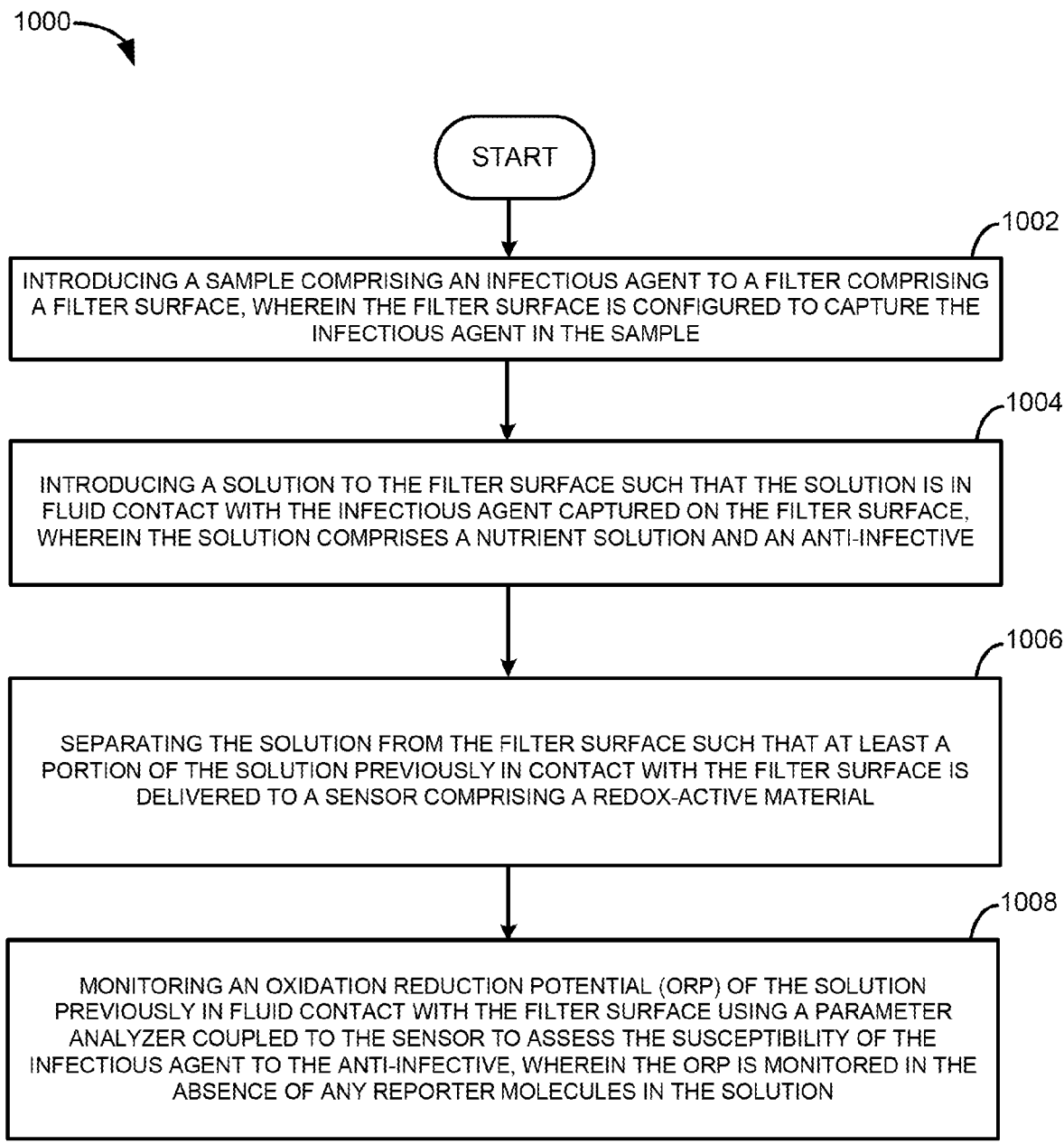
FIG. 10 illustrates yet another embodiment of a method for detecting a susceptibility of an infectious agent to one or more anti-infectives.

FIG. 10 illustrates a further embodiment of a method 1000 for detecting a susceptibility of an infectious agent 102 to one or more anti-infectives 106. The method 1000 can involve introducing a sample 104 comprising an infectious agent 102 to a filter 112 comprising a filter surface 126, wherein the filter surface 126 is configured to capture the infectious agent 102 in the sample 104 in step 1002. The method 1000 can also involve introducing a solution 300 to the filter surface 126 such that the solution 300 is in fluid communication with the infectious agent 102 captured on the filter surface 126, wherein the solution 300 comprises nutrients and an anti-infective 106 in step 1004. The method 100 can further involve separating the solution 300 from the filter surface 126 such that at least a portion of the solution 300 previously in contact with the filter surface 126 is delivered to a sensor 114 comprising a redox-active material 508 in step 1006. The method 1000 can also involve monitoring an ORP of the solution 300 previously in fluid communication with the filter surface 126 using at least one parameter analyzer 120 coupled to the sensor 114 to assess the susceptibility of the infectious agent 102 to the anti-infective 106, wherein the ORP is monitored in the absence of any added or exogenous reporter molecules in the solution 300 in step 1008.

Figure 11:
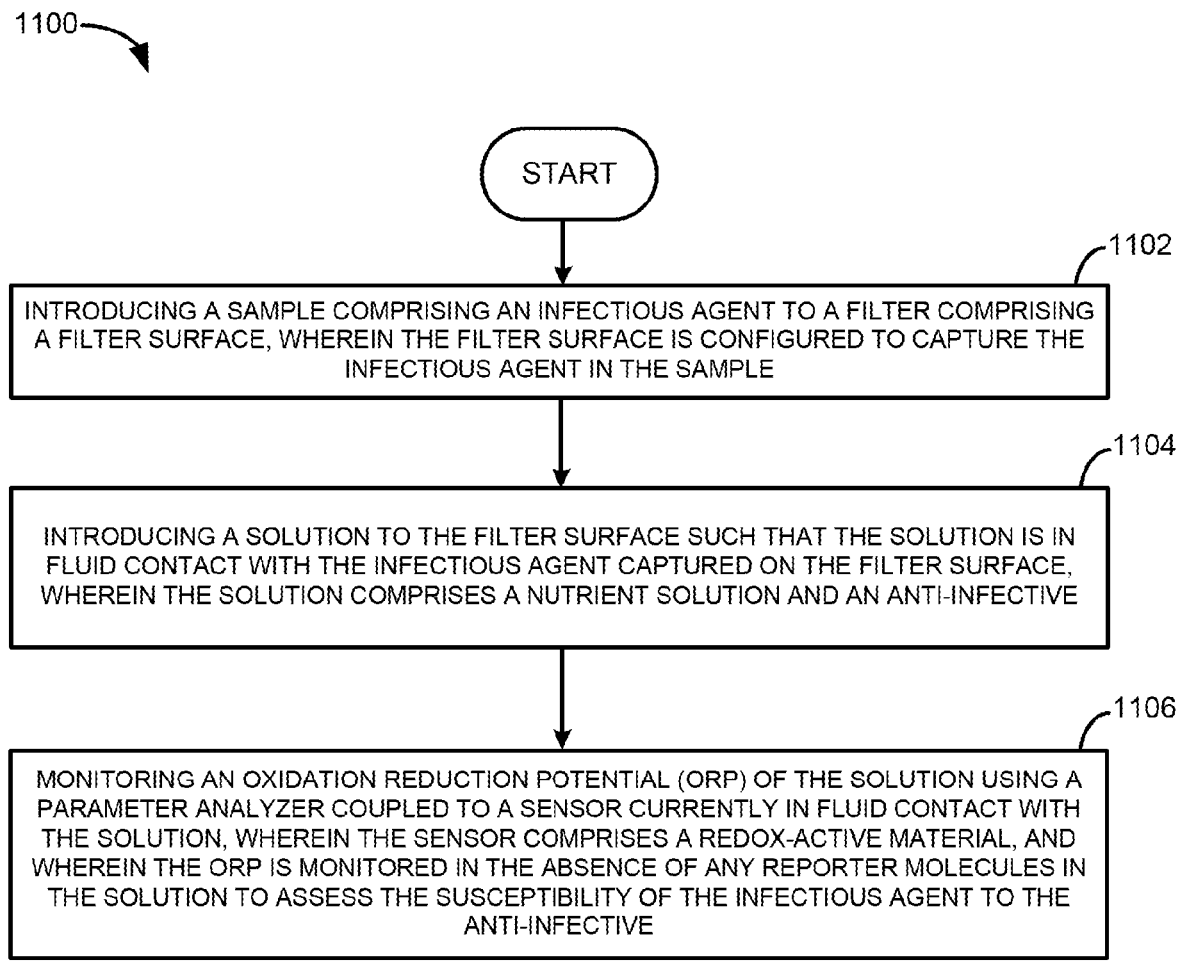
FIG. 11 illustrates a further embodiment of a method for detecting a susceptibility of an infectious agent to one or more anti-infectives.

FIG. 11 illustrates yet another embodiment of a method 1100 for detecting a susceptibility of an infectious agent 102 to one or more anti-infectives 106. The method 1100 can involve introducing a sample 104 comprising an infectious agent 102 to a filter 112 comprising a filter surface 126, wherein the filter surface 126 is configured to capture the infectious agent 102 in the sample 104 in step 1102. The method 1100 can also involve introducing a solution 300 to the filter surface 126 such that the solution 300 is in fluid communication with the infectious agent 102 captured on the filter surface 126, wherein the solution 300 comprises nutrients and an anti-infective 106 in step 1104. The method 1100 can further involve monitoring an ORP of the solution 300 using at least one parameter analyzer 120 coupled to a sensor 114 currently in fluid communication with the solution 300, wherein the sensor 114 comprises a redox-active material 508, and wherein the ORP is monitored in the absence of any added or exogenous reporter molecules in the solution 300 to assess the susceptibility of the infectious agent 102 to the anti-infective 106 in step 1106.

The flowcharts or process flows depicted in FIGS. 8-11 do not require the particular order shown to achieve the desired result and certain steps or processes may be omitted or may occur in parallel.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A system for detecting a susceptibility of one or more infectious agents to one or more anti-infectives, the system comprising:
 a first housing comprising a first surface, wherein the first surface is configured to receive an aliquot of a sample comprising one or more infectious agents in the sample;
 a second housing comprising a second surface, wherein the second surface is configured to receive another aliquot of the sample comprising one or more infectious agents in the sample;
 a first fluid delivery conduit configured to introduce a first solution to the first surface such that the first solution is in fluid communication with the one or more infectious agents on the first surface, wherein the first solution comprises a nutrient solution and one or more anti-infectives;
 a second fluid delivery conduit configured to introduce a second solution to the second surface such that the second solution is in fluid communication with the one or more infectious agents on the second surface, wherein the second solution comprises the nutrient solution and does not comprise the one or more anti-infectives;

a first sensor comprising a redox-active layer positioned on top of at least one conductive metallic layer, wherein the first sensor is coupled to the first housing such that the first sensor receives a portion of the first solution;

a second sensor comprising a redox-active layer positioned on top of at least one conductive metallic layer, wherein the second sensor is coupled to the second housing such that the second sensor receives a portion of the second solution; and one or more parameter analyzers coupled to the first sensor and the second sensor, wherein the one or more parameter analyzers are configured to monitor a first oxidation reduction potential (ORP) of the first solution in fluid communication with the first sensor and to monitor a second ORP of the second solution in fluid communication with the second sensor, wherein the first ORP is monitored in the absence of any added redox mediators or reporter molecules in the first solution, wherein the second ORP is monitored in the absence of any added redox mediators or reporter molecules in the second solution, and wherein the one or more parameter analyzers are configured to compare the first ORP with the second ORP to assess the susceptibility of the one or more infectious agents to the one or more anti-infectives.

2. The system of claim 1, wherein the first sensor comprises an active electrode and a reference electrode.

3. The system of claim 1, wherein the second sensor comprises an active electrode and a reference electrode.

4. The system of claim 1, wherein the redox-active layer comprises a gold layer, a platinum layer, a metal oxide layer, a carbon layer, or a combination thereof.

5. The system of claim 4, wherein the metal oxide layer comprises an iridium oxide layer, a ruthenium oxide layer, or a combination thereof.

6. The system of claim 1, wherein the sample comprises a biological sample, a bodily fluid, a wound swab or sample, a rectal swab or sample, a bacterial culture derived therefrom, or a combination thereof.

7. The system of claim 6, wherein the bodily fluid comprises urine, blood, sputum, saliva, breast milk, spinal fluid, semen, vaginal secretions, cerebrospinal fluid, synovial fluid, pleural fluid, peritoneal fluid, pericardial fluid, amniotic fluid, or a combination thereof.

8. The system of claim 1, wherein the one or more infectious agents comprise bacteria from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof.

9. The system of claim 1, wherein the one or more infectious agents comprises a fungus.

10. The system of claim 1, wherein the one or more anti-infectives comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, Amphotericin B, Flucytosine, Fluconazole, Ketoconazole, Itraconazole, Posaconazole, Ravuconazole, Voriconazole, or a combination thereof.

11. A system for detecting a susceptibility of one or more infectious agents to one or more anti-infectives, the system comprising:

a first housing configured to receive an aliquot of a sample comprising one or more infectious agents in the sample;

a second housing configured to receive another aliquot of the sample comprising one or more infectious agents in the sample;

a first fluid delivery conduit configured to introduce a first solution to the first housing such that the first solution is in fluid communication with the one or more infectious agents within the first housing, wherein the first solution comprises a nutrient solution and one or more anti-infectives;

a second fluid delivery conduit configured to introduce a second solution to the second housing such that the second solution is in fluid communication with the one or more infectious agents within the second housing, wherein the second solution comprises the nutrient solution and does not comprise the one or more anti-infectives;

a first sensor comprising a redox-active layer positioned on top of at least one conductive metallic layer, wherein the first sensor is coupled to the first housing such that the first sensor receives a portion of the first solution;

a second sensor comprising a redox-active layer positioned on top of at least one conductive metallic layer, wherein the second sensor is coupled to the second housing such that the second sensor receives a portion of the second solution; and one or more parameter analyzers coupled to the first sensor and the second sensor, wherein the one or more parameter analyzers are configured to monitor a first oxidation reduction potential (ORP) of the first solution in fluid communication with the first sensor and to monitor a second ORP of the second solution in fluid communication with the second sensor, wherein the first ORP is monitored in the absence of any added redox mediators or reporter molecules in the first solution, wherein the second ORP is monitored in the absence of any added redox mediators or reporter molecules in the second solution, and wherein the one or more parameter analyzers are configured to compare the first ORP with the second ORP to assess the susceptibility of the one or more infectious agents to the one or more anti-infectives.

12. The system of claim 11, wherein the first sensor comprises an active electrode and a reference electrode.

13. The system of claim 11, wherein the second sensor comprises an active electrode and a reference electrode.

14. The system of claim 11, wherein the redox-active layer comprises a gold layer, a platinum layer, a metal oxide layer, a carbon layer, or a combination thereof.

15. The system of claim 14, wherein the metal oxide layer comprises an iridium oxide layer, a ruthenium oxide layer, or a combination thereof.

16. The system of claim 11, wherein the sample comprises a biological sample, a bodily fluid, a wound swab or sample, a rectal swab or sample, a bacterial culture derived therefrom, or a combination thereof.

17. The system of claim 16, wherein the bodily fluid comprises urine, blood, sputum, saliva, breast milk, spinal fluid, semen, vaginal secretions, cerebrospinal fluid, synovial fluid, pleural fluid, peritoneal fluid, pericardial fluid, amniotic fluid, or a combination thereof.

18. The system of claim 11, wherein the one or more infectious agents comprise bacteria from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof.

19. The system of claim 11, wherein the one or more infectious agents comprises a fungus.

20. The system of claim 11, wherein the one or more anti-infectives comprise β-lactams, β-lactam and β-lactam inhibitor combinations, Aminoglycosides, Ansamycins, Carbapenems, Cephalosporins, Chloramphenicols, Glycopeptides, Fluoroquinolones, Lincosamides, Lincosamines, Lipopeptides, Macrolides, Monobactams, Nitrofurans, Oxazolidinones, Quinolones, Rifampins, Streptogramins, Sulfonamides, Tetracyclines, polypeptides, phages, Amphotericin B, Flucytosine, Fluconazole, Ketoconazole, Itraconazole, Posaconazole, Ravuconazole, Voriconazole, or a combination thereof.

* * * * *